United States Patent [19]

Kai et al.

[11] Patent Number: 5,188,747

[45] Date of Patent: Feb. 23, 1993

[54] FLUORINE-CONTAINING LUBRICANT COMPOUNDS

[75] Inventors: Yoshiaki Kai, Neyagawa; Takashi Suzuki, Takatsuki, both of Japan

[73] Assignee: Matsushita Electric Industrial Co., Ltd., Osaka, Japan

[21] Appl. No.: 672,447

[22] Filed: Mar. 20, 1991

[30] Foreign Application Priority Data

| Sep. 4, 1990 | [JP] | Japan | 2-234883 |
| Sep. 28, 1990 | [JP] | Japan | 2-260898 |
| Nov. 30, 1990 | [JP] | Japan | 2-337983 |

[51] Int. Cl.$^5$ ............................................ C10M 105/54
[52] U.S. Cl. ........................................ 252/54; 560/227; 560/195; 560/196; 560/197; 252/51
[58] Field of Search ................ 252/54, 51; 560/227, 560/195, 196, 197

[56] References Cited

U.S. PATENT DOCUMENTS

| 3,778,308 | 12/1973 | Roller et al. | 428/421 |
| 3,798,265 | 3/1974 | Bartlett | 562/567 |
| 3,935,277 | 1/1976 | Dear | 560/195 |
| 4,069,244 | 1/1978 | Mueller | 252/353 |
| 4,081,399 | 3/1978 | Dear | 252/356 |
| 4,084,059 | 4/1978 | Katsushima | 560/197 |
| 4,171,282 | 10/1979 | Mueller | 252/8.57 |
| 4,473,371 | 9/1984 | Schinzel | 560/197 |
| 4,525,305 | 6/1985 | Patel | 560/195 |

FOREIGN PATENT DOCUMENTS

| 0721328 | 11/1965 | Canada. |
| 0074057 | 3/1983 | European Pat. Off.. |
| 54-84524 | 7/1979 | Japan. |
| 60-109028 | 6/1985 | Japan. |
| 60-173096 | 9/1985 | Japan. |
| 61-24547 | 2/1986 | Japan. |
| 61-107527 | 5/1986 | Japan. |
| 61-107528 | 5/1986 | Japan. |
| 61-107529 | 5/1986 | Japan. |
| 61-257226 | 11/1986 | Japan. |
| 62-92225 | 4/1987 | Japan. |
| 62-92226 | 4/1987 | Japan. |
| 62-92227 | 4/1987 | Japan. |
| 1-70450 | 3/1989 | Japan. |

*Primary Examiner*—Jacqueline Howard
*Assistant Examiner*—Thomas Steinberg
*Attorney, Agent, or Firm*—Stevens, Davis, Miller & Mosher

[57] ABSTRACT

A fluorine-containing compound represented by the general formula [I]:

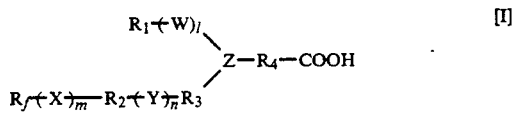

wherein $R_f$, X, Y, W, Z, $R_1$-$R_3$, l, m and n are as defined in the specifications. There are disclosed fluorine-containing compounds of specific structure which have in the molecule a fluoroalkyl ether end group, an aliphatic hydrocarbon end group and a carboxyl end group, and have molecular weights of hundreds to about 3,000; and a process for producing the fluorine-containing compounds. These fluorine-containing compounds can be utilized in magnetic recording media in the form of a lubricant composition.

20 Claims, No Drawings

FLUORINE-CONTAINING LUBRICANT COMPOUNDS

BACKGROUND OF THE INVENTION

1. Field of the Invention

The present invention relates to a novel fluorine-containing compound useful as a lubricant for precision machines and precision parts which require high-precision lubrication, or as a surfactant, a mold-release agent, a rust preventive, etc.; a process for producing the fluorine-containing compound; a lubricant composition comprising the fluorine-containing compound; and a magnetic recording medium such as a magnetic tape, a magnetic disk, etc., the lubricant layer of which comprises the fluorine-containing compound.

2. Description of the Prior Art

With minuaturization and an increase in precision of machines and parts thereof, the mode of lubrication in their sliding portions has come to be changed from hydrodynamic lubrication to boundary lubrication. Particularly in electronic machines and electronic parts, for example, VTR and magnetic discs, high-precision lubrication has become necessary for sliding a magnetic tape or a magnetic disc on a magnetic head, because of employment of thin ferromagnetic metal films for improving the packing density. For example, in metallized tapes and hard discs, a lubricant layer on the surface of a magnetic layer is formed to a thickness of only several tens angstroms to increase the output by reducing the loss due to the spacing between a magnetic recording medium and a magnetic head as much as possible while assuring the durability and the practical reliability. Therefore, it is an important problem to develop an organic compound having an excellent lubricating capability, as a material for forming the lubricant layer.

As lubricants for thin-metal-film type magnetic recording medium, those having a fluorocarbon chain in the molecule are excellent in compatibility with thin metal films, and hence there have been proposed various fluorocarbon-based lubricants (for instance, Japanese Patent Application Kokai Nos. 61-107527, 61-107528, 61-107529, 62-92225, 62-92226 and 62-92227). In addition, compounds comprising a perfluralkyl polyether chain have been proposed as lubricants for magnetic recording medium (for instance, U.S. Pat. No. 3,778,308 and Japanese Patent Application Kokai No. 60-109028).

On the other hand, fluorine-containing compounds having the molecular structure shown below have been proposed as surfactants:

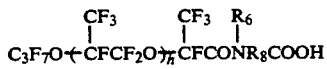

wherein $R_6$ is a hydrogen atom or an aliphatic alkyl group having 1 to 12 carbon atoms, $R_8$ is an aliphatic alkylene group having 1, 2 or 5 carbon atoms, and h is zero or an integer of 1 to 8 (U.S. Pat. No. 3,798,265).

The following is an important requirement which a lubricant for thin-metal-film type magnetic recording medium should satisfy. The lubricant should adhere strongly to the surface of the thin metal film or the protective film of the medium and the surface of a magnetic head to form a coating layer on each of the surfaces, and groups of molecules of the lubricant should easily be sheared from one another on the contact point of the coating layers, namely, on the surface on which the magnetic recording medium and the magnetic head slide.

Perfluoroalkyl polyethers heretofore well-known as lubricants for magnetic recording medium are good in the ease of shearing between groups of molecules because substantially the whole surface of each molecule is covered with fluorine atoms. But since the polarity of the molecules is low, the conventional lubricants have a low adhesive strength to the surface of a thin metal film or a protective film and the surface of a magnetic head. For removing this defect, there have been proposed perfluoroalkyl polyethers having various polar groups introduced into the ends of the molecule. But when their molecular weight is 3,000 or more, no sufficient effect of the introduction of the polar groups can be obtained. On the other hand, when the molecular weight is reduced for enhancing the effect of the polar groups, the interaction between molecules of the perfluoroalkyl polyether is weak, so that the amount of such a lubricant is decreased by its evaporation. Thus, the perfluoroalkyl polyethers and the terminally modified products thereof are poor in adhesive properties to the surface of a thin metal film or a protective film and the surface of a magnetic head, and in stability. Consequently, thin-metal-film type magnetic recording media obtained by using these compounds as lubricants have been poor in reliability on durability, in particular, in performance characteristics in low-humidity circumstances in which the aggregation of a magnetic metal tends to occur on the surface of a magnetic head.

On the other hand, the fluorocarbon-based lubricants disclosed in the above prior art references have heretofore been used in thin-metal-film type magnetic recording media because of their excellent compatibility with thin metal films, but have been disadvantageous in that they cannot give a sufficient durability in a low-humidity circumstance of 10% RH or less.

Conventional processes for producing a fluorine-containing compound are described below.

A process for producing a fluorine-containing alkyl-succinic acid derivative has been proposed in Japanese Patent Application Kokai No. 61-257226. Specifically, in this process, the fluorine-containing alkyl-succinic acid derivative is obtained by subjecting a mixture of equimolar amounts of a higher alcohol having a perfluoroalkyl group and alkylsuccinic anhydride to reaction with heating at 60° to 150° C. in the atmosphere. This process is effective against perfluoroalkyl group, but has been disadvantageous in that when an alcohol having a fluoroalkyl ether group is used in place of the higher alcohol having a perfluoroalkyl group, the yield of the fluorine-containing alkylsuccinic acid derivative is as very low as 10% or less because the reactivity of the former alcohol is considerably lower than that of the latter alcohol. Furthermore, this process has been disadvantageous also in that since the position of attachment of the fluoroalkyl ether end group to an aliphatic-alkylcarboxylic acid is limited to the carbon atom at the $\alpha$ or $\beta$ position adjacent to the carboxyl group, there cannot be obtained a fluorine-containing compound in which the fluoroalkyl ether end group is attached to any of various positions from $\alpha$ position to $\omega$ position.

A process for producing a nitrogen-containing perfluoro(carboxylic acid fluoride) has been proposed in Japanese Patent Application Kokai No. 64-70450. Specifically, in this process, a perfluoro(3-dialkylamino-n- butyric fluoride) is obtained by electrolyzing a reactive derivative of 3-dialkylamino-n-butyric acid in liquid hydrogen fluoride. This process has been disadvantageous not only in that both of the two aliphatic hydrocarbon end groups in the molecule of the product are perfluoroalkyl groups, but also in that it is difficult to utilize an aliphatic long-chain alkyl group or an aliphatic polyalkyl oxide group.

A process for producing a phthalic acid diester having a perfluorobutenyloxy group has been proposed in Japanese Patent Application Kokai No. 61-24547. Specifically, in this invention, the phthalic acid diester having a perfluorobutenyloxy group is obtained by adding 2 to 20 moles of an aliphatic alcohol having an alkyl group having 1 to 15 carbon atoms and 0.01 to 1 mole of concentrated sulfuric acid per mole of a phthalic anhydride derivative having a perfluorobutenyloxy group, and carrying out the reaction with refluxing the alcohol or at 100° to 150° C. for 30 minutes to 24 hours. This process has been disadvantageous not only in that both reactive groups of the acid anhydride becomes ester linkage groups, but also in that a fluoroalkyl ether group cannot be utilized because a fluoroalkyl group as the end group is limited to perfluorobutenyloxy group.

A process for producing a perfluoroalkyl-substituted half ester or a perfluoroalkyl-substituted half amide has been proposed in Japanese Patent Application Kokai No. 54-84524. Specifically, in this process, the perfluoroalkyl-substituted half ester or half amide is obtained by reacting maleic anhydride with a hydroxy-substituted or amino-substituted nonionic compound (e.g. an aliphatic alkyl alcohol or an aliphatic alkyl amine) at room temperature or at 50° to 100° C. to obtain a maleic acid half ester or a maleic acid half amide, and then adding a perfluoroalkylalkylene thiol to the thus obtained half ester or half amide at 30° to 75° C. in the presence of a base catalyst. The perfluoro-alkyl-substituted half ester or half amide can be obtained also by reversing the order of the above reactions. These processes have been disadvantageous in that the product obtained by them is a mixture of compounds having a thioether linkage group to the carbon atom at the α or β, respectively, position adjacent to the carboxyl group, so that there cannot be obtained a single fluorine-containing compound having a thioether linkage group only to the carbon atom at the α position.

SUMMARY OF THE INVENTION

An object of the present invention is to provide a novel fluorine-containing compound which imparts a high reliability on durability to thin-metal-film type magnetic recording media in all circumstances including low-humidity circumstances; a lubricant composition comprising the fluorine-containing compound; and a magnetic recording medium such as a magnetic tape, a magnetic disc, etc., the lubricant layer of which comprises the fluorine-containing compound.

In order to achieve this object, the present inventors conducted various researches in consideration of the problems in the prior art and consequently have found that a fluorine-containing compound having in the molecule a fluoroalkyl ether end group, an aliphatic hydrocarbon end group and a specific polar end group is most suitable as a lubricant for thin-metal-film type magnetic recording medium. The present invention was made on the basis of such finding and a novel production process.

The present invention relates to fluorine-containing compounds represented by the general formula [I]:

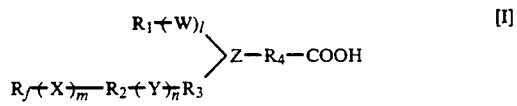

wherein $R_f$ is a fluoroalkyl ether end group having 5 to 50 carbon atoms, $R_1$ is an aliphatic alkyl end group or an aliphatic alkenyl end group, $R_2$ is an aliphatic alkylene group or an aliphatic polyalkylene oxide group which have no or one or more carbon atoms, each of $R_3$ and $R_4$ is an aliphatic alkylene group having no or one or more carbon atoms, X is a connecting group selected from the group consisting of $$—COOR_5— \text{ and } —CON(R_6)—$$

(wherein $R_5$ is an aliphatic alkylene group having no or one or more carbon atoms, and $R_6$ is a hydrogen atom or an aliphatic alkyl group having 1 to 12 carbon atoms), each of W and Y is a connecting group selected from the group consisting of $$—S—, —COO— \text{ and } —SCH_2CH(R_7)COO—$$

(wherein $R_7$ is a hydrogen atom or a methyl group), Z is a connecting group selected from the group consisting of

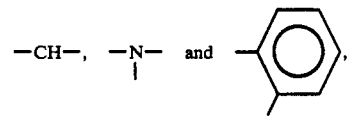

and each of l, m and n is zero or 1.

More specifically, the present invention relates to fluorine-containing compounds represented by the following general formulas [II], [III], and [VII] to [X]:

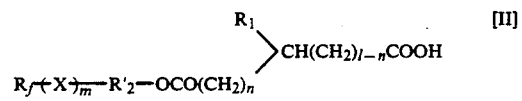

wherein $R_f$ is a fluoroalkyl ether end group having 5 to 50 carbon atoms, $R_1$ is an aliphatic alkyl end group or an aliphatic alkenyl end group, $R'_2$ is an aliphatic alkylene group or an aliphatic polyalkylene oxide group, X is a connecting group selected from the group consisting of $$—COOR_5— \text{ and } —CON(R_6)—$$

(wherein $R_5$ is an aliphatic alkylene group having no or one or more carbon atoms, and $R_6$ is a hydrogen atom or an aliphatic alkyl group having 1 to 12 carbon atoms), and each of m and n is zero or 1;

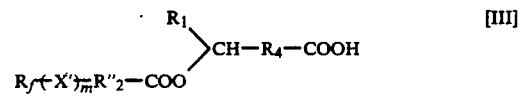

wherein $R_f$ is a fluoroalkyl ether end group having 5 to 50 carbon atoms, $R_1$ is an aliphatic alkyl end group or an aliphatic alkenyl end group, each of $R''_2$ and $R_4$ is an aliphatic alkylene group having no or one or more carbon atoms, X' is a connecting group selected from the group consisting of $$-COOR'_5- \text{ and } -CON(R_6)-$$

(wherein R'$_5$ is an aliphatic alkylene group, and R$_6$ is a hydrogen atom or an aliphatic alkyl group having 1 to 12 carbon atoms), and m is zero or 1;

$$\begin{matrix} R_1 \\ R_f-R'''_2 \end{matrix} \!\!> N-R_4-COOH \quad [VII]$$

wherein R$_f$ is a fluoroalkyl ether end group having 5 to 50 carbon atoms, R$_1$ is an aliphatic alkyl end group or an aliphatic alkenyl end group, R'''$_2$ is an aliphatic alkylene group, and R$_4$ is an aliphatic alkylene group having no or one or more carbon atoms;

$$\begin{matrix} R_1-OCO \\ R_f(X)_m R'_2-OCO \end{matrix} \!\!> Z'-COOH \quad [VIII]$$

wherein R$_f$ is a fluoroalkyl ether end group having 5 to 50 carbon atoms, R$_1$ is an aliphatic alkyl end group or an aliphatic alkenyl end group, R'$_2$ is an aliphatic alkylene group or an aliphatic polyalkylene oxide group, X is a connecting group selected from the group consisting of $$-COOR_5- \text{ and } -CON(R_6)-$$

(wherein R$_5$ is an aliphatic alkylene group having no or one or more carbon atoms, and R$_6$ is a hydrogen atom or an aliphatic alkyl group having 1 to 12 carbon atoms), Z' is a connecting group represented by the formula:

<img: para-phenylene ring>, and m is zero or 1;

$$\begin{matrix} R'_1-S \\ R_f(X)_m R'_2-OCO(CH_2)_n \end{matrix} \!\!> CH(CH_2)_{1-n}COOH \quad [IX]$$

wherein R$_f$ is a fluoroalkyl ether end group having 5 to 50 carbon atoms, R'$_1$ is an aliphatic alkyl end group, R'$_2$ is an aliphatic alkylene group or an aliphatic polyalkylene oxide group, X is a connecting group selected from the group consisting of $$-COOR_5- \text{ and } -CON(R_6)-$$

(wherein R$_5$ is an aliphatic alkylene group having no one or more carbon atoms, and R$_6$ is a hydrogen atom or an aliphatic alkyl group having 1 to 12 carbon atoms), and each of m and n is zero or 1;

$$\begin{matrix} R'_1 \\ R_7 \\ R_f(X)_m R'_2-OCOCHCH_2-S \end{matrix} \!\!> CHCOOH \quad [X]$$

wherein R$_f$ is a fluoroalkyl ether end group having 5 to 50 carbon atoms, R'$_1$ is an aliphatic alkyl end group, R'$_2$ is an aliphatic alkylene group or an aliphatic polyalkylene oxide group, R$_7$ is a hydrogen atom or a methyl group, X is a connecting group selected from the group consisting of $$-COOR_5- \text{ and } -CON(R_6)-$$

(wherein R$_5$ is an aliphatic alkylene group having no or one or more carbon atoms, and R$_6$ is a hydrogen atom or an aliphatic alkyl group having 1 to 12 carbon atoms), and m is zero or 1.

DESCRIPTION OF THE PREFERRED EMBODIMENTS

The end groups of the fluorine-containing compounds of the present invention include, for example, the groups described below.

The aliphatic hydrocarbon end groups, i.e., the aliphatic alkyl end group and the aliphatic alkenyl end group, include, for example, $$C_iH_{2i+1}- \quad C_iH_{2i-1}- \quad C_iH_{2i+1}-\underset{\underset{C_jH_{2j+1}}{|}}{CH}-C_kH_{2k}-$$

wherein each of i and j is an integer of 6 or more, and k is zero or an integer of 1 or more. The number of carbon atoms of each of these end groups is suitably 6 to 30 (preferably 10 to 26). When it is 5 or less, or 31 or more, the lubricating properties are deteriorated.

The fluoroalkyl ether end group includes $$F(C_3F_6O)_p C_2F_4- \quad CF_3O(C_2F_4O)_p(CF_2O)_q CF_2-$$

$$F(CFCF_2O)_p CF- \underset{CF_3}{|} \underset{CF_3}{|}$$

$$CF_3O(CF_2CFO)_p(CF_2O)_q CF_2- \underset{CF_3}{|}$$

$$CClF_2O(CF_2CFO)_p(CF_2O)_q CF_2- \underset{CF_3}{|}$$

wherein p is an integer of 1 to 15, and q is an integer of 1 to 45. The number of carbon atoms of each of these end groups is suitably 50 or less (preferably 40 or less). When it is 51 or more, the effect of the polar end group is lessened.

Processes for producing the fluorine-containing compounds of the present invention are explained below.

A fluorine-containing compound of the general formula [II] can be produced in high yield by subjecting a mixture of equimolar amounts of an aliphatic-alkylsuccinic anhydride or an aliphatic-alkenylsuccinic anhydride and an alcohol having an fluoroalkyl ether group to addition reaction with heating at 100° to 150° C., at a pressure of 3 kg/cm² or more in an autoclave. As to this addition reaction, a conventional method in which the reaction is carried out at atmospheric pressure gives a very low yield. In the present invention, a high yield can be obtained by finding out a method in which as described above, the reaction is carried out under pressure. In this case, a pressure of at least 3 kg/cm$^2$ is required.

A fluorine-containing compound of the general formula [III] can be obtained by adding a carboxylic acid halide having a fluoroalkyl ether group to a mixed solution of an aliphatic-alkyl oxy-acid or an aliphatic-alkenyl oxy-acid and a base such as triethylamine or pyridine (as a solvent, the base itself or an aprotic anhydrous solvent such as anhydrous benzene or anhydrous ether is suitable) slowly with ice-cooling so as to make the amount of the acid halide equimolar with that of the oxy-acid, subjecting the reactive group of the acid halide and the hydroxyl group of the oxy-acid to esterification, and capturing and removing secondarily produced hydrochloric acid by means of the base.

As to a method for attaching a fluoroalkyl ether group to the hydroxyl group of an oxy-acid, when esterification is carried out by the use of a carboxylic acid having a fluoroalkyl ether group and a conventional acid catalyst at a high temperature, the carboxyl group of the oxy-acid inhibits this reaction, so that the fluoroalkyl group cannot be attached to the hydroxyl group of the oxy-acid. Thus, the present inventors have found that this esterification can be allowed to proceed only by a method in which a carboxylic acid halide having a fluoroalkyl group is used and the reaction is carried out at a low temperature. This finding enabled the production of the fluorine-containing compound of the present invention.

A fluorine-containing compound of the general formula [VII] can be produced by adding an aqueous solution of an weak alkali such as sodium carbonate or potassium carbonate to a mixed solution of equimolar amounts of a secondary alkylamine having a fluoroalkyl ether group and a w-haloalkylcarboxylic acid ester (as a solvent, a hydrophilic solvent such as acetone or methyl ethyl ketone is suitable), refluxing the resulting mixture with heating to induce dehalogention and nitrogen-carbon bonding reaction, and then subjecting the ester linkage group to hydrolysis with a strong alkali to make one of the end groups into a carboxyl group. In the dehalogenation, a carboxyl group inhibits the attack of the $\omega$-haloalkyl group against the imino group because of its high affinity for the imino group. Thus, the present inventors have found that since the presence of a carboxyl group inhibits the dehalogenation, the nitrogen-carbon bonding reaction can be allowed to proceed by masking the carboxyl group, for example, by subjecting the carboxyl group to esterification. This finding also enabled the production of the fluorine-containing compound of the present invention.

A fluorine-containing compound of the general formula [VIII] can be produced by adding an alcohol having a fluoroalkyl ether group to a mixed solution of trimellitic anhydride chloride and a base such as triethylamine or pyridine (as a solvent, the base itself or an aprotic anhydrous solvent such as anhydrous benzene or anhydrous ether is suitable) slowly with ice-cooling so as to make the amount of the alcohol equimolar with that of trimellitic anhydride chloride, capturing and removing secondarily produced hydrochloric acid by means of the base to obtain a trimellitic anhydride fluoroalkyl ether ester, adding to the ester an alcohol having an aliphatic hydrocarbon group in an amount equimolar with the amount of the ester and an aprotic anhydrous solvent such as anhydrous benzene or anhydrous n-heptane, refluxing the resulting mixture with heating at 70° to 140° C. to subject the reactive group of the acid anhydride to ester-addition reaction with the alcohol having an aliphatic hydrocarbon group. The esterification of the trimellitic anhydride chloride is carried out by subjecting the reactive group of acid anhydride to a second-stage reaction after subjecting the reactive group of acid chloride to a first-stage reaction. By these reaction, different alcohol moieties can be introduced into the same molecule through ester linkages. Moreover, one of the carbonyl groups, i.e., the reactive groups of acid anhydride becomes carboxyl end group. Thus, the present inventors have found that in the second-stage reaction, the alcohol attached through an ester linkage by the first-stage reaction does not undergo hydrolysis and transesterification. This finding also enabled the production of the fluorine-containing compound of the present invention.

A fluorine-containing compound of the general formula [IX] can be produced in high yield by subjecting a mixture of equimolar amounts of thiomalic anhydride having an aliphatic alkyl group and an alcohol having a fluoroalkyl ether group to addition reaction with heating at 100° to 150° C., at a pressure of 3 kg/cm$^2$ or more in an autoclave. As to this addition reaction, a conventional method in which the reaction is carried out at atmospheric pressure gives a very low yield. In the present invention, a high yield can be obtained by finding out a method in which, as described above, the reaction is carried out under pressure. In this case, a pressure of at least 3 kg/cm$^2$ is required.

A fluorine-containing compound of the general formula [X] can be produced by adding a base catalyst such as sodium acetate, triethylamine, or pyridine and a polymerization inhibitor such as hydroquinone to a mixed solution of equimolar amounts of a $\alpha$-mercapto aliphatic-alkylcarboxylic acid and an acrylate or a methacrylate which have a fluoroalkyl ether group (as a solvent, a hydrophilic solvent such as ethanol or methyl ethyl ketone is suitable), and refluxing the resulting mixture with heating to add a group having a carbon-carbon double bond, i.e., an acryl or methacryl group to the mercapto group. The addition reaction of an aliphatic-alkylthiol to an aliphatic-alkylolefin has heretofore been well known [as literature on this reaction, there is, for example, "Yuki lo Kagaku-Gosei Hanno Hen (Organic sulfur Chemistry-Synthetic Reaction)" p. 33, Kagaku Dojin K.K., (1982)]. The present inventor have found that also when an $\alpha$-mercapto aliphatic-alkylcarboxylic acid is used as a thiol, the above addition reaction proceeds without inhibition by the carboxyl group. This finding also enabled the production of the fluorine-containing compound of the present invention.

As the starting fluoroalkyl ethers used for producing the fluorine-containing compounds of the present invention, there are, for example, the compounds described below.

The alcohol having a fluoroalkyl ether group includes, for example,

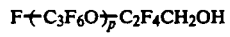

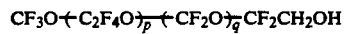

-continued $$F\text{-}(CFCF_2O)_{\overline{p}}CFCH_2OH$$
with $CF_3$ groups on each CF $$F\text{-}(CFCF_2O)_{\overline{p}}CFCH_2OCO(CH_2)_3OH$$
with $CF_3$ groups $$F\text{-}(CFCF_2O)_{\overline{p}}CFCH_2OCO(CH_2)_4OH$$
with $CF_3$ groups $$F\text{-}(CFCF_2O)_{\overline{p}}CFCONR'''_2OH$$
with $CF_3$, $CF_3$, $R_6$ groups $$F\text{-}(CFCF_2O)_{\overline{p}}CFCO\text{-}(OC_2H_4)_{\overline{r}}OH$$
with $CF_3$ groups $$F-(CFCF_2O)_{\overline{p}}CFCO\text{-}(OC_3H_6)_{\overline{r}}OH$$
with $CF_3$ groups $$CF_3O\text{-}(CF_2CFO)_{\overline{p}}\text{-}(CF_2O)_{\overline{q}}CF_2CH_2OH$$
with $CF_3$ group $$CClF_2O\text{-}(CF_2CFO)_{\overline{p}}\text{-}(CF_2O)_{\overline{q}}CF_2CH_2OH$$
with $CF_3$ group wherein $R_6$ is a hydrogen atom or an aliphatic alkyl group having 1 to 12 carbon atoms, $R'''_2$ is an aliphatic alkylene group, p is an integer of 1 to 15, q is an integer of 1 to 45, and r is an integer of 1 or more.

The carboxylic acid halide having a fluoroalkyl ether group includes, for example, $$F\text{-}(C_3F_6O)_{\overline{p}}C_2F_4COX$$

$$CF_3O\text{-}(C_2F_4O)_{\overline{p}}\text{-}(CF_2O)_{\overline{q}}CF_2COX$$

$$F\text{-}(CFCF_2O)_{\overline{p}}CFCOX$$
with $CF_3$ groups $$F\text{-}(CFCF_2O)_{\overline{p}}CFCH_2OCO(CH_2)_2COX$$
with $CF_3$ groups $$F\text{-}(CFCF_2O)_{\overline{p}}CFCH_2OCO(CH_2)_3COX$$
with $CF_3$ groups $$F\text{-}(CFCF_2O)_{\overline{p}}CFCONR'''_2COX$$
with $CF_3$, $CF_3$, $R_6$ groups $$CF_3O\text{-}(CF_2CFO)_{\overline{p}}\text{-}(CF_2O)_{\overline{q}}CF_2COX$$
with $CF_3$ group $$CClF_2O\text{-}(CF_2CFO)_{\overline{p}}\text{-}(CF_2O)_{\overline{q}}CF_2COX$$
with $CF_3$ group wherein $R_6$ is a hydrogen atom or an aliphatic alkyl group having 1 to 12 carbon atoms, $R'''_2$ is an aliphatic alkylene group, X is a fluorine atom or a chlorine atom, p is an integer of 1 to 15, and q is an integer of 1 to 45.

The secondary alkylamine having a fluoroalkyl ether group includes, for example, $$F\text{-}(C_3F_6O)_{\overline{p}}C_2F_4CH_2NHR_1$$

$$CF_3O\text{-}(C_2F_4O)_{\overline{p}}\text{-}(CF_2O)_{\overline{q}}CF_2CH_2NHR_1$$

$$F\text{-}(CFCF_2O)_{\overline{p}}CFCH_2NHR_1$$
with $CF_3$, $CF_3$ groups $$CF_3O\text{-}(CF_2CFO)_{\overline{p}}\text{-}(CF_2O)_{\overline{q}}CF_2CH_2NHR_1$$
with $CF_3$ group $$CClF_2O\text{-}(CF_2CFO)_{\overline{p}}\text{-}(CF_2O)_{\overline{q}}CF_2CH_2NHR_1$$
with $CF_3$ group wherein $R_1$ is an aliphatic alkyl end group or an aliphatic alkenyl end group, p is an integer of 1 to 15, and q is an integer of 1 to 45.

The acrylate having a fluoroalkyl ether group includes, for example, $$F\text{-}(C_3F_6O)_{\overline{p}}C_2F_4CH_2OCOCH=CH_2$$

$$CF_3O\text{-}(C_2F_4O)_{\overline{p}}\text{-}(CF_2O)_{\overline{q}}CF_2CH_2OCOCH=CH_2$$

$$F\text{-}(CFCF_2O)_{\overline{p}}CFCH_2OCOCH=CH_2$$
with $CF_3$, $CF_3$ groups $$F\text{-}(CFCF_2O)_{\overline{p}}CFCH_2OCO(CH_2)_3OCOCH=CH_2$$
with $CF_3$, $CF_3$ groups $$F\text{-}(CFCF_2O)_{\overline{p}}CFCH_2OCO(CH_2)_4OCOCH=CH_2$$
with $CF_3$, $CF_3$ groups $$F\text{-}(CFCF_2O)_{\overline{p}}CFCONR'''_2OCOCH=CH_2$$
with $CF_3$, $CF_3$, $R_6$ groups $$F\text{-}(CFCF_2O)_{\overline{p}}CFCO\text{-}(OC_2H_4)_{\overline{r}}OCOCH=CH_2$$
with $CF_3$, $CF_3$ groups $$F\text{-}(CFCF_2O)_{\overline{p}}CFCO\text{-}(OC_3H_6)_{\overline{r}}OCOCH=CH_2$$
with $CF_3$, $CF_3$ groups $$CF_3O\text{-}(CF_2CFO)_{\overline{p}}\text{-}(CF_2O)_{\overline{q}}CF_2CH_2OCOCH=CH_2$$
with $CF_3$ group $$CClF_2O\text{-}(CF_2CFO)_{\overline{p}}\text{-}(CF_2O)_{\overline{q}}CF_2CH_2OCOCH=CH_2$$
with $CF_3$ group wherein $R_6$ is a hydrogen atom or an aliphatic alkyl group having 1 to 12 carbon atoms, $R'''_2$ is an aliphatic alkylene group, p is an integer of 1 to 15, q is an integer of 1 to 45, and r is an integer of 1 or more.

The methacrylate having a fluoroalkyl ether group includes, for example, $$F\text{-}(C_3F_6O)_{\overline{p}}C_2F_4CH_2OCOC(CH_3)=CH_2$$

$$CF_3O\text{-}(C_2F_4O)_{\overline{p}}\text{-}(CF_2O)_{\overline{q}}CF_2CH_2OCOC(CH_3)=CH_2$$

$$F\text{-}(CFCF_2O)_{\overline{p}}CFCH_2OCOC(CH_3)=CH_2$$
with $CF_3$, $CF_3$ groups -continued

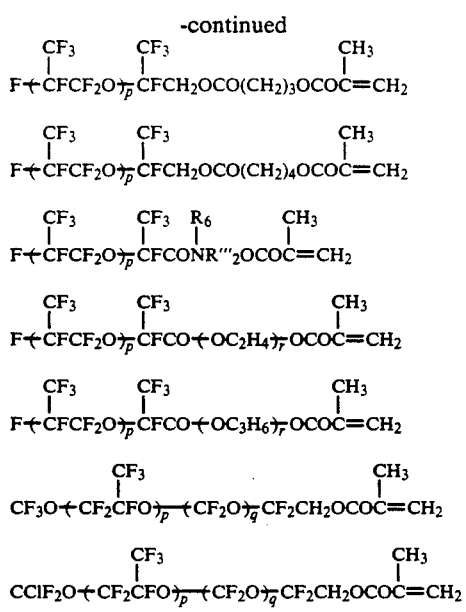

wherein $R_6$ is a hydrogen atom or an aliphatic alkyl group having 1 to 12 carbon atoms, $R'''_2$ is an aliphatic alkylene group, p is an integer of 1 to 15, q is an integer of 1 to 45, and r is an integer of 1 or more.

As the lubricant compositions of the present invention, mixtures of a fluorine-containing compound of the general formula [I] and another lubricant are suitable. As the another lubricant, fluorocarbon type lubricants are preferably used. The fluorine-containing compound of the general formula [I] can be used alone as an lubricant. In particular, the fluorocarbon type lubricants described, for example, in Japanese Patent Application Kokai Nos. 61-107527, 61-107528, 61-107529, 62-92225, 62-92226 and 62-92227 are suitable. In addition, other conventional lubricants, rust preventives, etc. can be used in admixture with the fluorine-containing compound of the general formula [I].

The fluorine-containing compound of the general formula [I] should be contained in the lubricant composition in a proportion of 20% or more, preferably 30% or more. When its content is less than 20%, the effect of the present invention can hardly be obtained.

Next, there are explained below examples of thin ferromagnetic-metal-film type magnetic recording medium obtained by forming a lubricant layer comprising the fluorine-containing compound of the general formula [I].

The above-mentioned lubricant composition is applied on the magnetic layer of a thin-ferromagnetic-metal-film type magnetic recording medium directly or with a protective layer between by a conventional wet coating method or a dry coating method such as vacuum deposition. As to the amount of coating, the composition is applied in the form of a thin layer in an amount of 0.05 to 100 mg, preferably 0.1 to 50 mg, per $m^2$ of the surface.

As the thin ferromagnetic metal film, there can be used thin films of Co, Co-Ni, Co-Cr, Co-Fe, Co-Ni-Cr, Co-Ni-Fe, Co-Ni-P, Co-Ni-Ta and the like, and a partially oxidized product thereof. These thin films are formed by vacuum deposition, sputtering, ion plating, plating, etc. If necessary, a primer layer of Cr, Ti or the like can be formed. The thickness of the thin ferromagnetic metal film including the thickness of the primer layer is suitably 500 to 5,000 Å. On the surface of the thin ferromagnetic metal film, there can optionally be formed, for example, a metallic protective layer of Cr, W, NiP or the like; an inorganic protective layer of SiO, SiC, carbon, graphite, diamond-like carbon or the like; an organic protective layer of a fluororesin, silicone resin, epoxy resin, polyamide resin, plasma polymerization product, radiation polymerization product or the like; or a composite protective layer.

As a non-magnetic substrate, there can be used those composed mainly of an oxide such as glass, ceramics or the like; a metal such as Al alloy, Ti alloy or the like; or a plastic such as polyester, polyimide, polyamide-imide, polycarbonate, polyacrylate or the like. In addition, there can be used substrates obtained by optionally forming a Co-P plated film, a polyimide coating film or the like on the surface of any of these materials, and substrates obtained by optionally forming, for example, protuberances in the form of fine particles, hills, waves or the like, or by texturing. The surface roughnness of the substrates is suitably 50 to 600 Å in terms of maximum height (R max.). As their shape, for example tape, film, sheet, disc, card and drum shapes can be chosen depending on purposes.

The fluorine-containing compounds of the present invention have in the molecule a fluoroalkyl ether end group, an aliphatic hydrocarbon end group and a specific polar end group, and their molecular weight is hundreds to about 3,000. Therefore, the effect of the polar end group is sufficiently brought about and the polar end group adheres strongly to the surface of the thin metal film or the protective film and the surface of a magnetic head. In addition, the fluoroalkyl ether end group is exposed at the surface of the lubricant layer to contribute to the reduction of the surface energy and make the surface not adhesive. Furthermore, the aliphatic hydrocarbon end group has a flexible carbon-carbon chain, and molecules of the compound are oriented by the moderate intermolecular interaction with the hydrocarbon chains of adjacent molecules, so that the compound has satisfactory lubricating properties.

Accordingly, by virtue of these synergistic effects of the end groups, a satisfactory lubricating capability is exhibited in all circumstances including low-humidity circumstances. Therefore, the problems in the reliability on durability of a thin-metal-film type magnetic recording medium are solved.

As described above, the fluorine-containing compounds of the present invention can be utilized not only singly but also in the form of a lubricant composition comprising a mixture of the fluorine-containing compound and a conventional compound. Moreover, they can be utilized for producing a magnetic recording medium comprising a lubricant layer comprising the fluorine-containing compound. Therefore, their industrial value is very high.

In Examples 1 to 49, there are specifically described examples of fluorine-containing compound and processes for producing the same. In Examples 50 to 112, there are specifically described examples of magnetic recording medium obtained by using a lubricant composition comprising each of the fluorine-containing compounds.

However, the present invention should not be construed to be restricted by these examples.

EXAMPLE 1

Production of

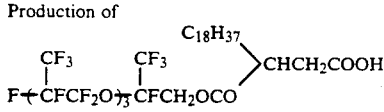

and

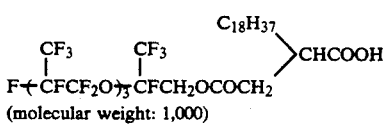

(molecular weight: 1,000)

In a 1-liter pressure autoclave made of glass having an agitating blade were placed 64.8 g (0.10 mole) of an alcohol having a fluoroalkyl ether group represented by the formula $F\text{---}(CF(CF_3)CF_2O)_3CF(CH_3)CH_2OH$ and 35.3 g (0.10 mole) of octadecylsuccinic anhydride. The air in the system was replaced with nitrogen, after which the reaction was carried out with stirring at 120° C. and at a nitrogen pressure of 3 kg/cm² for 5 hours. Then, the reaction mixture was dissolved in isopropyl ether, and the resulting solution was cooled to −10° C. to remove the unreacted octadecylsuccinic anhydride. Subsequently, the residue was transferred to a vacuum distillation still provided with an oil diffusion pump and the unreacted alcohol having a fluoroalkyl ether group was removed under conditions of 100° C. and about $1 \times 10^{-3}$ mmHg to obtain 92 g (yield 92%) of a white solid having a melting point of 86° C. As a result of infrared spectroscopic analysis (IR), gel permeation chromatography (GPC) and field desorption mass spectrometry (FD-MS), the while solid was found to be a mixture of fluorine-containing compounds of the formulas A and A' which did not contain the starting materials and any by-product.

IR: There appeared an absorption peak due to a carboxylic acid at 1,705 cm⁻¹ and an absorption peak due to an ester at 1,755 cm⁻¹. An absorption peak due to the acid anhydride at 1,775 cm⁻¹ disappeared.

GPC: There were not detected the starting materials, i.e., the alcohol having a fluoroalkyl ether group and octadecylsuccinic anhydride.

FD-MS: A parent peak appeared at a m/e ratio of 1,000.

EXAMPLE 2

Production of

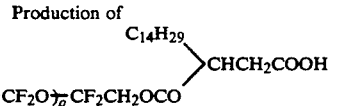

and

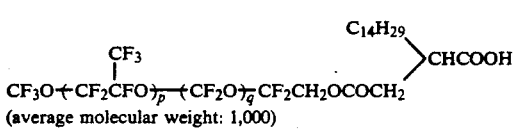

(average molecular weight: 1,000)

In a 1-liter pressure autoclave made of glass having an agitating blade were placed 70.0 g (0.10 mole) of an alcohol having a fluoroalkyl ether group represented by the formula $CF_3O\text{---}(CF_2CF(CF_3)O)_p[CF_2O]_qCF_2CH_2OH$ wherein each of p and q is an integer of 1 to 9 (average molecular weight: 700) and 29.7 g (0.10 mole) of tetradecylsuccinic anhydride. The air in the system was replaced with nitrogen, after which the reaction was carried out with stirring at 100° C. and at a nitrogen pressure of 5 kg/cm² for 6 hours. Then, the resulting mixture was dissolved in isopropyl ether and the resulting solution was cooled to −10° C. to remove the unreacted tetradecylsuccinic anhydride. Subsequently, the residue was transferred to a vacuum distillation still provided with an oil diffusion pump, and the unreacted alcohol having a fluoroalkyl ether group was removed under conditions of 100° C. and about $1 \times 10^{-3}$ mmHg to obtain 96 g (yield 96%) of a white solid having a melting point of 60° C. As a result of IR, GPC and FD-MS, the white solid was found to be a mixture of fluorine-containing compounds of the formulas B and B' which did not contain the starting materials and any by-product.

IR: There appeared an absorption peak due to a carboxylic acid at 1,705 cm⁻¹ and an absorption peak due to an ester at 1,755 cm⁻¹. An absorption peak due to the acid halide at 1,775 cm⁻¹ disappeared.

GPC: There were not detected the starting materials, i.e., the alcohol having a fluoroalkyl ether group and tetradecylsuccinic anhydride.

FD-MS: A parent peak appeared at a m/e ratio of 1,000.

EXAMPLE 3

Production of

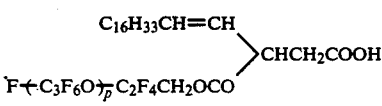

and

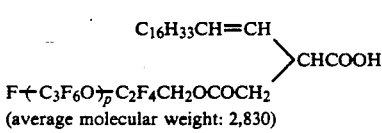

(average molecular weight: 2,830)

In a 1-liter pressure autoclave made of glass having an agitating blade were placed 248 g (0.10 mole) of an alcohol having a fluoroalkyl ether group represented by the formula $F\text{---}(C_3F_6O)_pC_2F_4CH_2OH$ wherein p is an integer of 1 to 15 (average molecular weight: 2,480) and 35.0 g (0.10 mole) of octadecenylsuccinic anhydride. The air in the system was replaced with nitrogen, after which the reaction was carried out with stirring at 140° C. and at pressure of 10 kg/cm² for 8 hours. Then, the reaction mixture was dissolved in isopropyl ether and the resulting solution was cooled to −10° C. to remove the unreacted octadecenylsuccinic anhydride. Subsequently, the residue was transferred to a vacuum distillation still provided with an oil diffusion pump and the unreacted alcohol having a fluoroalkyl ether group was removed under conditions of 140° C. and about $1 \times 10^{-4}$ mmHg to obtain g (yield 82%) of a wax-like semisolid. As a result of IR, GPC and FD-MS, the wax-like semisolid was found to be a mixture of fluorine-containing compounds of the formulas C and C' which did not contain the starting materials and any by-product.

IR: There appeared an absorption peak due to a carboxylic acid at 1,705 cm⁻¹ and an absorption peak due to an ester at 1,755 cm⁻¹. An absorption peak due to the acid anhydride at 1,775 cm⁻¹ disappeared.

GPC: There were not detected the starting materials, i.e., the alcohol having a fluoroalkyl ether group and octadecenylsuccinic anhydride.

FD-MS: A parent peak appeared at a m/e ratio of 2,830.

EXAMPLE 4

Production of

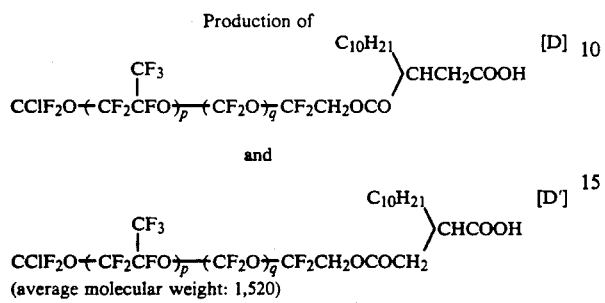

(average molecular weight: 1,520)

132 Grams (yield 87%) of a colorless and transparent liquid was produced under the same conditions as in Example 1, except for using 128 g (0.10 mole) of an alcohol having a fluoroalkyl ether group represented by the formula $CClF_2O+CF_2CF(CF_3)O]_p[CF_2O]_qCF_2C-H_2OH$ wherein each of p and q is an integer of 1 to 15 (average molecular weight: 1,280) and 24.0 g (0.10 mole) of decylsuccinic anhydride as starting materials. As a result of IR, GPC and FD-MS, the colorless and transparent liquid was found to be a mixture of fluorine-containing compounds of the formulas D and D which did not contain the starting materials and any by-product.

IR: There appeared an absorption peak due to a carboxylic acid at 1,750 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group and decylsuccinic anhydride.

FD-MS: A parent peak appeared at a m/e ratio of 1,520.

EXAMPLE 5

The following fluorine-containing compounds were produced under the same conditions as in Example 1.

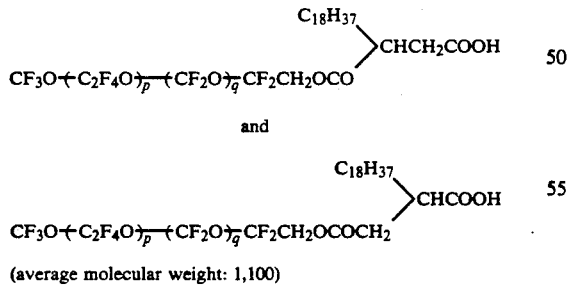

and

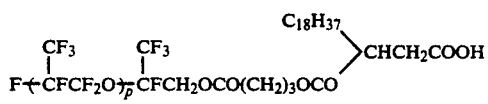

(average molecular weight: 1,100)

EXAMPLE 6

The following fluorine-containing compounds were produced under the same conditions as in Example 1.

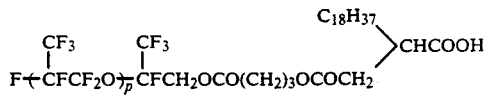

and

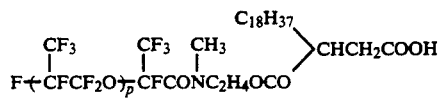

(average molecular weight: 1,730)

EXAMPLE 7

The following fluorine-containing compounds were produced under the same conditions as in Example 1.

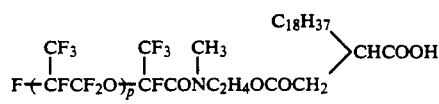

and

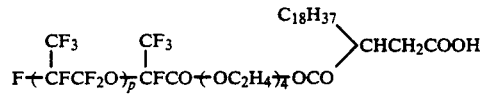

(average molecular weight: 1,250)

EXAMPLE 8

The following fluorine-containing compounds were produced under the same conditions as in Example 1.

and

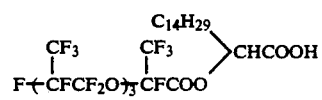

(average molecular weight: 1,750)

EXAMPLE 9

Production of

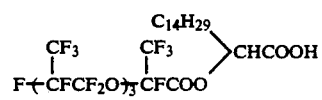 [E]

(molecular weight: 917)

In a 1-liter flask equipped with an agitating blade and a dropping funnel were placed 66.4 g (0.10 mole) of a carboxylic acid fluoride having a fluoroalkyl ether group represented by the formula $F+CF(CF_3)C-F_2O]_3CF(CF_3)COF$ and 300 ml of anhydrous diethyl ether, and cooled to 5° C. or lower. Then, a solution of 27.2 g (0.10 mole) of α-hydroxypalmitic acid in 100 ml of anhydrous pyridine was added dropwise with stirring over a period of about 2 hours to carry out the reaction. After completion of the reaction, the reaction solution was washed with 5% hydrochloric acid. Subsequently, it was repeatedly washed with distilled water until the pH of the aqueous layer became 7. The solution thus washed was dried over anhydrous sodium sulfate. Then, the resulting solution was cooled to −10° C. to remove the unreacted α-hydroxypalmitic acid. The residue was transferred to a vacuum distillation still provided with an oil diffusion pump, and a carboxylic acid having a fluoroalkyl ether group produced from the unreacted starting carboxylic acid fluoride having a fluoroalkyl ether group by hydrolysis was removed under conditions of 100° C. and about $1 \times 10^{-3}$ mmHg to obtain 60 g of a white solid having a melting point of 76° C. As a result of IR, GPC and FD-MS, the white solid was found to be a fluorine-containing compound of the formula E which did not contain the starting materials and any by-product.

IR: An absorption peak due to an ester at 1,755 cm$^{-1}$ appeared. An absorption peak due to a hydroxyl group at 3,330 cm$^{-1}$ disappeared.

GPC: There were not detected the carboxylic acid having a fluoroalkyl ether group and α-hydroxy-palmitic acid, the starting materials.

FD-MS: A parent peak appeared at a m/e ratio of 917.

EXAMPLE 10

Production of

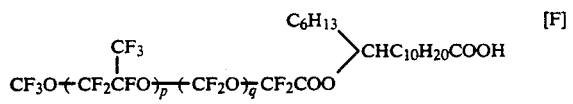

[F]

(average molecular weight: 1,010)

In a 1-liter flask equipped with an agitating blade and a dropping funnel were placed 75.0 g (0.10 mole) of a carboxylic acid chloride having a fluoroalkyl ether group represented by he formula CF$_3$O$+$CF$_2$CF(CF$_3$)O$\}_p$$\{$CF$_2$O$\}_q$CF$_2$COCl wherein each of p and q is an integer of 1 to 9 (average molecular weight: 750) and 300 ml of anhydrous diethyl ether, and cooled to 5° C. or lower. Then, a solution of 30.1 g (0.10 mole) of 12-hydroxystearic acid in 100 ml of anhydrous pyridine was added dropwise with stirring over a period of about 2 hours to carry out the reaction. After completion of the reaction, the same purifying treatment as in Example 9 was carried out to obtain a white solid (72 g) having a melting point of 62° C. As a result of IR, GPC and FD-MS, the white solid was found to be a fluorine containing compound of the formula F which did not contain the starting materials and any by-product.

IR: An absorption peak due to an ester at 1,755 cm$^{-1}$ appeared. An absorption peak due to a hydroxyl group at 3,330 cm$^{-1}$ disappeared.

GPC: There were not detected carboxylic acid having a fluoroalkyl ether group and 12-hydroxystearic acid, the starting materials.

FD-MS: A parent peak appeared at a m/e ratio of 1,010.

EXAMPLE 11

Production of

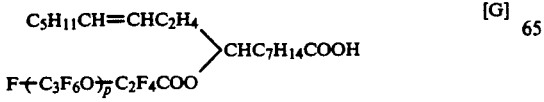

[G]

(average molecular weight: 2,770)

In a 1-liter flask equipped with an agitating blade and a dropping funnel were placed 30.0 g (0.10 mole) of 9-oxy-12-octadecencic acid and 300 ml of anhydrous pyridine, and cooled to 5° C. or lower. Then, a solution prepared by dissolving 251 g (0.10 mole) of a carboxylic acid chloride having a fluoroalkyl ether group represented by the formula F$+$C$_3$F$_6$O$\}_p$C$_2$F$_4$COCl wherein p is an integer of 1 to 15 (average molecular weight: 2,510) in 300 ml of anhydrous diethyl ether, was added dropwise with stirring over a period of about 3 hours to carry out the reaction. After completion of the reaction, the same purifying treatment as in Example 9 was carried out to obtain a wax-like semisolid (166 g). As a result of IR, GPC and FD-MS, the wax-like semisolid was found to be a fluorine-containing compound of the formula G which did not contain the starting materials and any by-product.

IR: An absorption peak due to an ester at 1,755 cm$^{-1}$ appeared. An absorption peak due to a hydroxyl group at 3,330 cm$^{-1}$ disappeared.

GPC: There were not detected carboxylic acid having a fluoroalkyl ether group and 9-oxy-12-octadecenoic acid, the starting materials.

FD-MS: A parent peak appeared at a m/e ratio of 2,770.

EXAMPLE 12

Production of

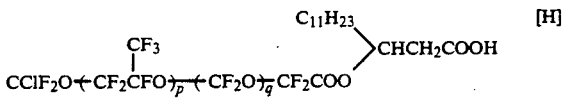

[H]

(average molecular weight: 1,550)

A colorless and transparent liquid was produced under the same conditions as in Example 9, except for using a carboxylic acid chloride having a fluoroalkyl ether group represented by the formula CClF$_2$O$+$CF$_2$CF(CF$_3$)O$\}_p$$\{$CF$_2$COCl wherein each of and q is an integer of 1 to 15 (average molecular weight: 1,310) and β-hydroxymyristic acid as starting materials. As a result of IR, GPC and FD-MS, the colorless and transparent liquid was found to be a fluorine-containing compound of the formula H which did not contain the starting materials and any by-product.

IR: An absorption peak due to an ester at 1,755 cm$^{-1}$ appeared. An absorption peak due to a hydroxyl group at 3,330 cm$^{-1}$ disappeared.

GPC: There were not detected carboxylic acid having a fluoroalkyl ether group and β-hydroxymyristic acid, the starting materials.

FD-MS: A parent peak appeared at a m/e ratio of 1,550.

EXAMPLE 13

The following fluorine-containing compound was produced under the same conditions as in Example 9.

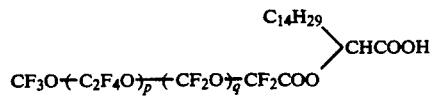

(average molecular weight: 1,010)

EXAMPLE 14

The following fluorine-containing compound was produced under the same conditions as in Example 9.

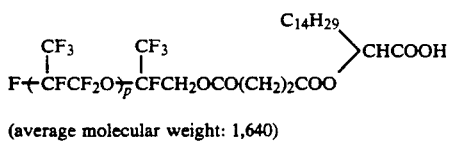

(average molecular weight: 1,640)

EXAMPLE 15

The following fluorine-containing compound was produced under the same conditions as in Example 9.

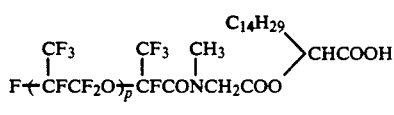

(average molecular weight: 1,360)

EXAMPLE 16

Production of

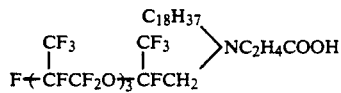 [J]

(molecular weight: 972)

In a 1-liter flask equipped with an agitating blade and a dropping funnel were placed 90.0 g (0.10 mole) of a secondary alkylamine having a fluoroalkyl ether group represented by the formula F$\{$CF(CF$_3$)C-F$_2$O$\}_3$CF(CF$_3$)CH$_2$NHC$_{18}$H$_{37}$, 21.4 g (0.10 mole) of methyl 3-iodopropionate and 300 ml of methyl ethyl ketone (MEK). A solution of 15.9 g of sodium carbonate in 100 ml of distilled water was added dropwise with stirring over a period of about 1 hour while raising the temperature. Then, refluxing and stirring were continued for another 8 hours to complete the reaction. After completion of the reaction, the MEK was removed from the reaction solution by distillation, and hexane was added to the residue to obtain a solution. This solution was repeatedly washed with distilled water until the pH of the aqueous layer became 7. The washed solution was dried over anhydrous sodium sulfate. Next, the hexane was distilled off and the residue was dissolved in isopropyl ether (IEP). The resulting solution was cooled to 5° C. to remove the unreacted secondary alkylamine having a fluoroalkyl ether group. Then, the IPE was distilled off and the residue was dissolved in methanol. The resulting solution was cooled to 0° C. to remove the unreacted methyl 3-iodopropionate. In a 1-liter flask equipped with an agitating blade and a dropping funnel were placed 59.2 g (0.06 mole) of the thus obtained methyl ester of fluorine-containing compound of the formula J and a solution of 13.0 g of sodium hydroxide in 150 ml of 90% ethanol. Refluxing and stirring were continued for 3 hours, after which 6 N hydrochloric acid was added until the reaction solution became acidic, whereby a precipitate was formed. The precipitate was dissolved in chloroform and the resulting solution was repeatedly washed with distilled water until the pH of the aqueous layer became 7. The washed solution was dried over anhydrous sodium sulfate. Then, the chloroform was distilled off, after which hexane was added to the residue to obtain a solution of the reaction product in hexane, and recrystallization was carried out at room temperature to obtain 52 g of a white solid having a melting point of 110° C. As a result of IR, GPC and FD-MS, the white solid was found to be the fluorine-containing compound of the formula J which did not contain the starting materials and any by-product.

IR: An absorption peak due to a carboxylic acid at 1,710 cm$^{-1}$ appeared.

GPC: There were not detected the stating materials, i.e., the secondary alkylamine having a fluoroalkyl ether group and methyl 3-iodopropionate.

FD-MS: A parent peak appeared at a m/e ratio of 972.

EXAMPLE 17

Production of

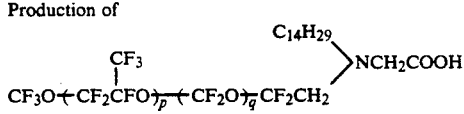 [K]

(average molecular weight: 950)

In a 1-liter flask equipped with an agittting blade and a dropping funnel were placed 89.0 g (0.10 mole) of a secondary alkylamine having a fluoroalkyl ether group represented by the formula CF$_3$O$\{$CF$_2$CF(CF$_3$)O$\}_p$[CF$_2$O]$_q$CF$_2$CH$_2$NHC$_{14}$H$_{29}$ wherein each of p and q is an integer of 1 to 9 (average molecular weight: 890), 20.0 g (0.10 mole) of methyl iodoacetate and 300 ml of MEK. A solution of 15.9 g of sodium carbonate in 100 ml of distilled water was added dropwise with stirring over a period of about 1 hour while raising the temperature. Then, refluxing and stirring were continued for another 8 hours to complete the reaction. After completion of the reaction, the same purifying treatment as in Example 16 was carried out. In a 1-liter flask equipped with an agitating blade and a dropping funnel were placed 57.7 g (0.06 mole) of the thus obtained methyl ester of a fluorine-containing compound of the formula K and a solution of 13.0 g of sodium hydroxide in 150 ml of 90% ethanol. Refluxing and stirring were conducted for 3 hours, after which 6 N hydrochloric acid was added dropwise until the reaction solution became acidic, whereby a precipitate was formed. The precipitate was subjected to the same purifying treatment as in Example 16 to obtain 50 g of a white solid having a melting point of 85° C. As a result of IR, GPC and FD-MS, the white solid was found to be the fluorine-containing compound of the formula K which did not contain the starting materials and any by-product.

IR: An absorption peak due to a carboxylic acid at 1,710 cm$^{-1}$ appeared.

GPC: There were not detected the starting materials, i.e., the secondary alkylamine having a fluoroalkyl ether group and methyl iodoacetate.

FD-MS: A parent peak appeared at a m/e ratio of 950.

EXAMPLE 18

Production of

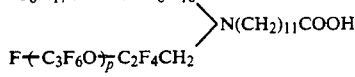
$$\begin{matrix} C_8H_{17}CH=CHC_8H_{16} \\ F\mathord{+}C_3F_6O\mathord{)}_pC_2F_4CH_2 \end{matrix} \Big\rangle N(CH_2)_{11}COOH \qquad [L]$$

(average molecular weight: 2,930)

A wax-like semisolid was obtained by the same production process as in Example 16, except for using a secondary alkylamine having a fluoroalkyl ether group represented by the formula $F\mathord{+}C_3F_6O\mathord{)}_pC_2F_4CH_2NHC_{18}H_{35}$ wherein p is an integer of 1 to 15 (average molecular weight: 2,730) and methyl 12-bromododecanoate as starting materials. As a result of IR, GPC and FD-MS, the wax-like semisolid was found to be a fluorine-containing compound of the formula L which did not contain the starting materials and any by-product.

IR: An absorption peak due to a carboxylic 1710 cm$^{-1}$ appeared.

GPC: There were not detected the starting materials, i.e., the secondary alkylamine having a fluoroalkyl alkyl ether group and methyl 12-bromododecanoate.

FD-MS: A main peak appeared at a m/e ratio of 2930.

EXAMPLE 19

Production of

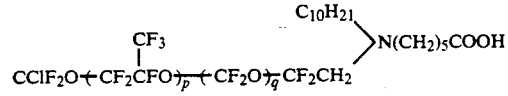
$$\begin{matrix} CF_3 & C_{10}H_{21} \\ CClF_2O\mathord{+}CF_2CFO\mathord{)}_p\mathord{+}CF_2O\mathord{)}_qCF_2CH_2 \end{matrix} \Big\rangle N(CH_2)_5COOH \qquad [M]$$

(average molecular weight: 1,530)

A wax-like semisolid was obtained by the same production process as in Example 16, except for using a secondary alkylamine having a fluoroalkyl ether group represented by the formula $CClF_2O\mathord{+}CF_2CF(CF_3)O\mathord{]}_p[CF_2O]_qCF_2CH_2NHC_{10}H_{21}$ wherein each of p and q is an integer of 1 to 15 (average molecular weight: 1,420) and methyl 6-iodohexanoate as starting materials. As a result of IR, GPC and FD-MS, the wax-like semisolid was found to be a fluorine-containing compound of the formula M which did not contain the starting materials and any by-product.

IR: An absorption peak due to a carboxylic acid at 1,710 cm$^{-1}$ appeared.

GPC: There were not detected the starting materials, i.e., the secondary alkylamine having a fluoroalkyl ether group and methyl 6-iodohexanoate.

FD-MS: A parent peak appeared at a m/e ratio of 1,530.

EXAMPLE 20

Production of

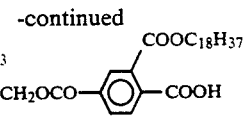

$$F\mathord{+}CFCF_2O\mathord{)}_3CFCH_2OCO\text{—}\underset{CF_3}{\overset{CF_3}{|}}\text{—C}_6H_3(COOC_{18}H_{37})\text{COOH} \qquad [N]$$

and

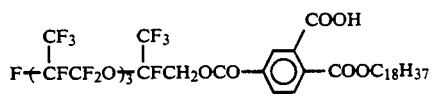

$$F\mathord{+}CFCF_2O\mathord{)}_3CFCH_2OCO\text{—}\underset{CF_3}{\overset{CF_3}{|}}\text{—C}_6H_3(COOH)(COOC_{18}H_{37}) \qquad [N']$$

(molecular weight: 1,093)

In a 1-liter flask equipped with an agitating blade and a dropping funnel were placed 21.2 g (0.10 mole) of trimellitic anhydride chloride and 300 ml of anhydrous pyridine, and cooled to 5° C. or lower. Then, a solution of 64.8 g (0.10 mole) of an alcohol having a fluoroalkyl ether group represented by the formula $F\mathord{+}CF(CF_3)CF_2O\mathord{]}_3CF(CF_3)CH_2OH$ in 300 ml of anhydrous diethyl ether was added dropwise with stirring over a period of about 3 hours to carry out the reaction. After completion of the reaction, the reaction solution was washed with 5% hydrochloric acid. Then, it was repeatedly washed with distilled water until the pH of the aqueous layer became 7. The solution thus washed was dried over anhydrous sodium sulfate. Subsequently, the diethyl ether was distilled off, after which the residue was transferred to a vacuum distillation still provided with an oil diffusion pump, and the unreacted starting alcohol having a fluoroalkyl ether group was removed under conditions of 100° C. and about $1 \times 10^{-3}$ mmHg to obtain 72.0 g of trimellitic anhydride fluoroalkyl ether ester. In a 1-liter flask equipped with an agitating blade were placed 72.0 g (0.088 mole) of this product, 23.8 g (0.088 mole) of stearyl alcohol and 300 ml of anhydrous benzene, and refluxed with heating to carry out the reaction. After completion of the reaction, the reaction solution was allowed to stand at room temperature for 24 hours to recrystallize the reaction product. The reaction product was further recrystallized from acetone to obtain a white solid (67 g) having a melting point of 42° C. As a result of IR, GPC and FD-MS, the white solid was found to be a mixture of fluorine-containing compounds of the formulas N and N' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid halide at 1,755 cm$^{-1}$ disappeared.

GPC: There were not detected the starting materials, i.e., the alcohol having fluoroalkyl ether group, stearyl alcohol, and chloride of trimellitic anhydride, and any by-product.

FD-MS: A parent peak appeared at a m/e ratio of 1,093.

EXAMPLE 21

Product of

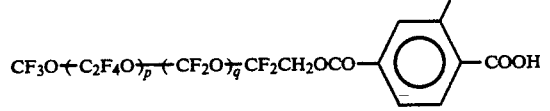

$$CF_3O\mathord{+}C_2F_4O\mathord{)}_p\mathord{+}CF_2O\mathord{)}_qCF_2CH_2OCO\text{—}C_6H_3(COOC_{18}H_{35})\text{COOH} \qquad [O]$$

and

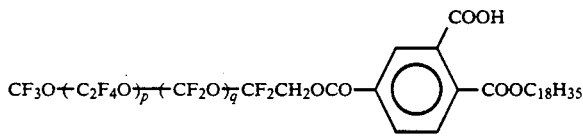

[O']

(average molecular weight: 1,200)

A wax-like semisolid was obtained by the same production process as in Example 20, except for using as starting materials an alcohol having a fluoroalkyl ether group represented by the formula $CF_3O(C_2F_4O)_p(CF_2O)_qCF_2CH_2OH$ wherein each of p and q is an integer of 1 to 7 (average molecular weight: 760), oleyl alcohol, and trimellitic anhydride chloride. As a result of IR, GPC and FD-MS, the wax-like semisolid was found to be a mixture of fluorine-containing compounds of the formulas O and O' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group, oleyl alcohol, and chloride of trimellitic anhydride, and any by-product.

FD-MS: A parent peak appeared at a m/e ratio of 1,200.

EXAMPLE 22

Production of

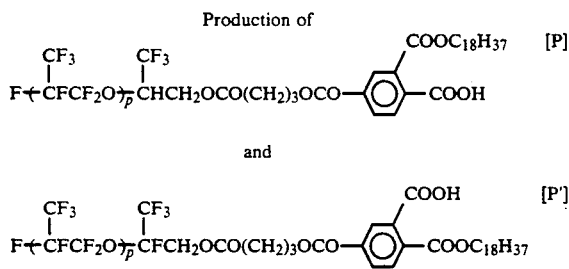

(average molecular weight: 1,830)

A wax-like semisolid was obtained by the same production process as in Example 20, except for using as starting materials an alcohol having a fluoroalkyl ether group represented by the formula $F(CF(CF_3)CF_2O)_pCF(CF_3)CH_2OCO(CH_2)_3OH$ wherein p is an integer of 1 to 15 (average molecular weight: 1,390), stearyl alcohol, and trimellitic anhydride chloride. As a result of IR, GPC and FD-MS, the wax-like semisolid was found to be a mixture of fluorine-containing compounds of the formulas P and P' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group, stearyl alcohol, and chloride of trimellitic anhydride, and any by-product.

EXAMPLE 23

Production of

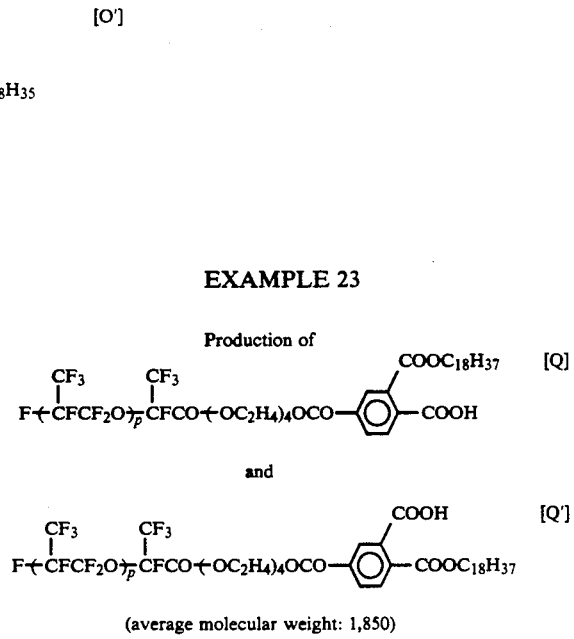

(average molecular weight: 1,850)

A wax-like semisolid was obtained by the same production process as in Example 20, except for using as starting materials an alcohol having a fluoroalkyl ether group represented by the formula $F(CF(CF_3)CF_2O)_pCF(CF_3)CO(OC_2H_4)_4OH$ wherein p is an integer of 1 to 15 (average molecular weight: 1,330), stearyl alcohol, and trimellitic anhydride chloride. As a result of IR, GPC and FD-MS, the wax-like semisolid was found to be a mixture of fluorine-containing compounds of the formulas Q and Q' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group, stearyl alcohol, and chloride of trimellitic anhydride, and any by-product.

EXAMPLE 24

The following fluorine-containing compounds were produced under the same conditions as in Example 20.

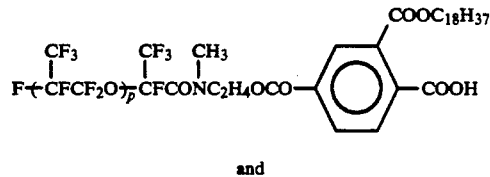

and

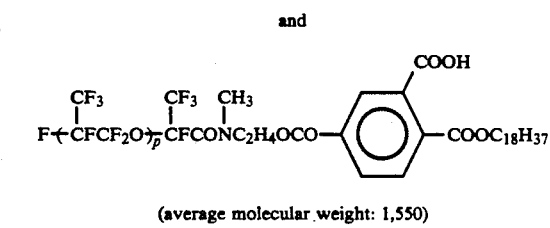

(average molecular weight: 1,550)

EXAMPLE 25

The following fluorine-containing compounds were produced under the same conditions as in Example 20.

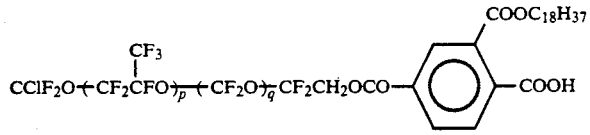

and

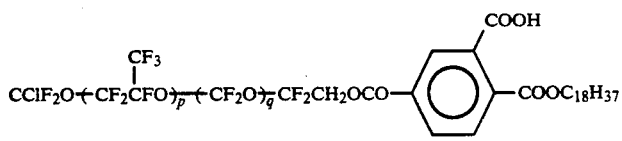

(average molecular weight: 1,770)

EXAMPLE 26

The following fluorine-containing compounds were produced under the same conditions as in Example 20.

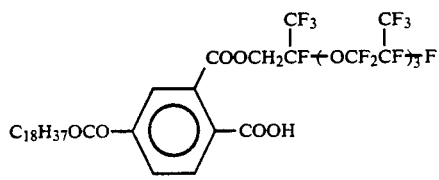

and

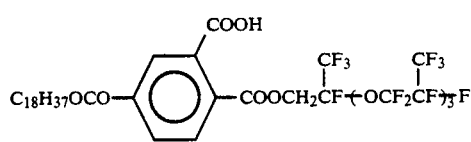

(molecular weight: 1,093)

EXAMPLE 27

The following fluorine-containing compounds were produced under the same conditions as in Example 20.

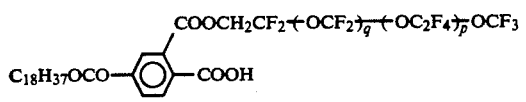

and

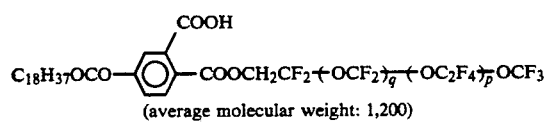

(average molecular weight: 1,200)

EXAMPLE 28

The following fluorine-containing compounds were produced under the same conditions as in Example 20.

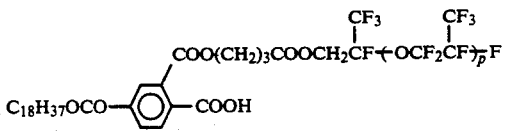

and (average molecular weight: 1,830)

EXAMPLE 29

The following fluorine-containing compounds were produced under the same conditions as in Example 20.

and (average molecular weight: 1,550)

EXAMPLE 30

The following fluorine-containing compounds were produced under the same conditions as in Example 20.

and

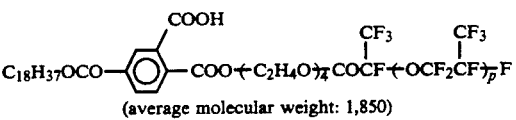

(average molecular weight: 1,850)

EXAMPLE 31

Production of

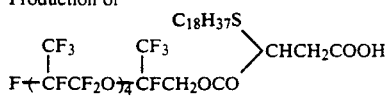 [R]

and

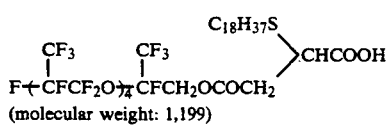 [R']

(molecular weight: 1,199)

In a 1-liter pressure autoclave made of glass having an agitating blade were placed 81.4 g (0.10 mole) of an alcohol having a fluoroalkyl ether group represented by the formula $F\text{-}(CF(CF_3)CF_2O)_{\overline{n}}CF(CF_3)CH_2OH$ and 38.5 g (0.10 mole) of octadecylthiomalic anhydride. The air in the system was replaced with nitrogen, after which the reaction was carried out with stirring for 10 hours at 120° C. and at a nitrogen pressure of 4 to 5 kg/cm$^2$. After completion of the reaction, the reaction mixture was dissolved in isopropyl ether and the resulting solution was cooled to $-10°$ C. to remove the unreacted octadecylthiomalic anhydride. Then, the residue was transferred to a vacuum distillation still produced with an oil diffusion pump, and the unreacted alcohol having a fluoroalkyl ether group was removed under conditions of 110° C. and about $1 \times 10^{-3}$ mmHg to obtain 102 g (yield 85%) of a white solid. As a result of IR, GPC and FD-MS, the white solid was found to be a mixture of fluorine-containing compounds of the formulas R and R' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group and octadecylthiomalic anhydride.

FD-MS: A parent peak appeared at a m/e ratio of 1,199.

EXAMPLE 32

Production of

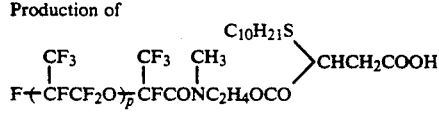 [S]

and

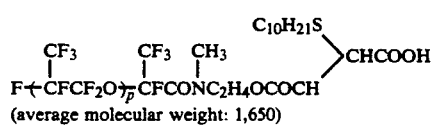 [S']

(average molecular weight: 1,650)

In a 1-liter pressure autoclave made of glass having an agitating blade were placed 138 g (0.10 mole) of an alcohol having a fluoroalkyl ether group represented by the formula $F\text{-}(CF(CF_3)CF_2O)_{\overline{p}}CF(CF_3)CON(CH_3)C_2H_4OH$ wherein p is an integer of 1 to 15 (average molecular weight: 1,380) and 27.2 g (0.10 mole) of decylthiomalic anhydride. The air in the system was replaced with nitrogen, after which the reaction was carried out with stirring for 5 hours at 140° C. and at a nitrogen pressure of 9 to 10 kg/cm$^2$. After completion of the reaction, the same purifying treatment as in Example 31 was carried out to obtain 129 g (yield 78%) of a milk-white colloidal liquid. As a result of IR, GPC and FD-MS, the milk-white colloidal liquid was found to be a mixture of fluorine-containing compounds of the formulas S and S' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid halide at 1,775 cm$^{-1}$ disappeared.

GPC: There were not detected the starting materials i.e., the alcohol having a fluoroalkyl ether group and decylthiomalic anhydride.

FD-MS: A parent peak appeared at a m/e ratio of 1,650.

EXAMPLE 33

Production of

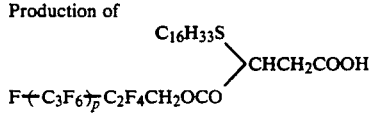 [T]

and

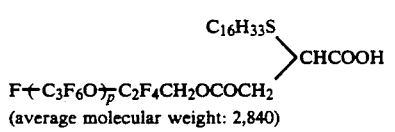 [T']

(average molecular weight: 2,840)

There was obtained about 204 g (yield 72%) of a milk-white colloidal liquid by the same production process as in Example 31, except for using 248 g (0.10 mole) of an alcohol having a fluoroalkyl ether group represented by the formula $F\text{-}(C_3F_6O)_{\overline{p}}C_2F_4CH_2OH$ wherein p is an integer of 1 to 15 (average molecular weight: 2,480) and 35.7 g (0.10 mole) of hexadecylthiomalic anhydride as starting materials. As a result of IR, GPC and FD-MS, the milk-white colloidal liquid was found to be a mixture of fluorine-containing compounds of the formulas T and T' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid anhydride at 1,775 cm$^{-1}$ disappeared.

GPC: There were not detected the starting materials, i.e., the alcohol having a fluoroalkyl ether group and hexadecylthiomalic anhydride.

FD-MS: A parent peak appeared at a m/e ratio of 2,840.

EXAMPLE 34

Production of

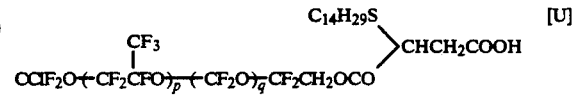 [U]

and

 [U']

-continued
(average molecular weight: 1,610)

There was obtained 134 g (yield 83%) of a milk-white colloidal liquid by the same production process as in Example 31, except for using 128 g (0.10 mole) of an alcohol having a fluoroalkyl ether group represented by the formula $CClF_2O\text{-}\!\!+\!\!CF_2CF(CF_3)O\!\!+_p\!\!+\!\!CF_2O\!\!+_q\!\!CF_2CH_2OH$ wherein each of p and q is an integer of 1 to 15 (average molecular weight: 1,280) and 32.9 g (0.10 mole) of tetradecylthiomalic anhydride as starting materials. As a result of IR, GPC and FD-MS, the milk-white colloidal liquid was found to be a mixture of fluorine-containing compounds of the formulas U and U' which did not contain the starting materials and any by-product.

IR: There appeared an absorption peak due to a carboxylic acid at 1,705 cm$^{-1}$ and an absorption peak due to an ester at 1,755 cm$^{-1}$. An absorption peak due to the acid halide at 1,775 cm$^{-1}$ disappeared.

GPC: There were not detected to starting materials, i.e., the alcohol having a fluoroalkyl ether group and tetradecylthiomalic anhydride.

FD-MS: A parent peak appeared at a m/e ratio of 1,610.

EXAMPLE 35

The following fluorine-containing compounds were produced under the same conditions as in Example 31.

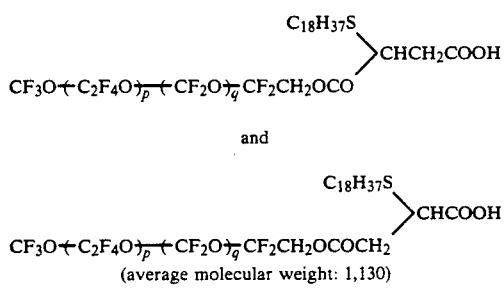

(average molecular weight: 1,130)

EXAMPLE 36

The following fluorine-containing compounds were produced under the same conditions as in Example 31.

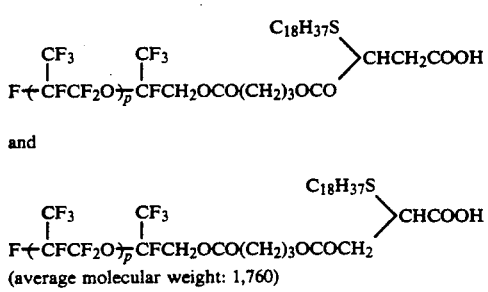

(average molecular weight: 1,760)

EXAMPLE 37

The following fluorine-containing compounds were produced under the same conditions as in Example 31.

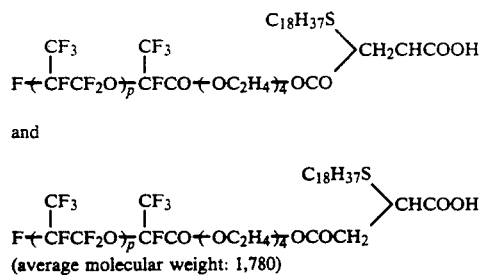

(average molecular weight: 1,780)

EXAMPLE 38

Production of

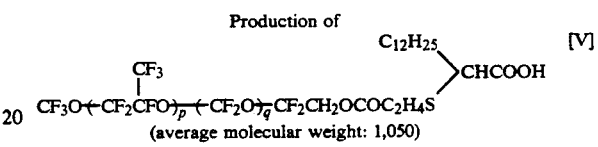

(average molecular weight: 1,050)

In a 1-liter flask equipped with an agitating blade were placed 79.0 g (0.10 mole) of an acrylate having a fluoroalkyl ether group represented by the formula $CF_3O\text{-}\!\!+\!\!CF_2CF(CF_3)O\!\!+_p\!\!+\!\!CF_2O\!\!+_q\!\!CF_2CH_2OCOCH=CH_2$ wherein each of p and q is an integer of 1 to 9 (average molecular weight: 790), 26.0 g (0.10 mole) of α-mercaptomyristic acid, 50 g of sodium acetate, 1 g of hydroquinone and 300 ml of 95% ethanol. They were subjected to addition reaction by continuing refluxing with heating for 6 hours. After completion of the reaction, the ethanol and the unreacted acrylate having a fluoroalkyl ether group were removed by vacuum distillation. Distilled water was added to the residue and the reaction product was extracted and purified with isopropyl ether to obtain 86 g of a white solid having a melting point of 35° C. As a result of IR, GPC and FD-MS, the white solid was found to be a fluorine-containing compound of the formula V which did not contain the starting materials and any by-product.

IR: There appeared an absorption peak due to a carboxylic acid at 1,705 cm$^{-1}$ and an absorption peak due to an ester at 1,755 cm$^{-1}$. There disappeared an absorption peak due to the thiol at 2,600 cm$^{-1}$ and an absorption peak due to a carbon-carbon double bond at 1,640 cm$^{-1}$.

GPC: There were not detected the starting materials, i.e., the acrylate having a fluoroalkyl ether group and α-mercaptomyristic acid.

FD-MS: A parent peak appeared at a m/e ratio of 1,050.

EXAMPLE 39

Production of

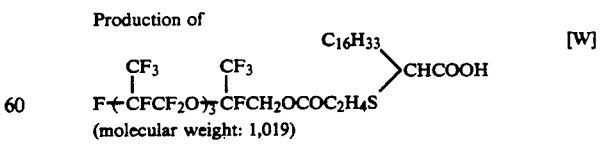

(molecular weight: 1,019)

In a 1-liter flask equipped with an agitating blade were placed 70.2 g (0.10 mole) of an acrylate having a fluoroalkyl ether group represented by the formula $F\text{-}\!\!+\!\!CF(CF_3)CF_2O\!\!+_3\!\!CF(CF_3)CH_2OCOCH=CH_2$ molecular weight: 702), 31.7 g (0.10 mole) of α-mercaptostearic acid, 50 g of sodium acetate, 1 g of hydroquinone and 300 ml of 95% ethanol. They were subjected to addition reaction by continuing refluxing with heating for 4 hours. After completion of the reaction, the same purifying treatment as in Example 38 was carried out to obtain 81 g of a white solid having a melting point of 79° C. As a result of IR, GPC and FD-MS, the white solid was found to be a fluorine-containing compound of the formula W which did not contain the starting materials and any by-product.

IR: There appeared an absorption peak due to a carboxylic acid at 1,705 cm$^{-1}$ and an absorption peak due to an ester at 1,755 cm$^{-1}$. There disappeared an absorption peak due to the thiol at 2,600 cm$^{-1}$ and an absorption peak due to a carbon-carbon double bond at 1,640 cm$^{-1}$.

GPC: There were not detected the starting materials, i.e., the acrylate having a fluoroalkyl ether group and α-mercaptostearic acid.

FD-MS: A parent peak appeared at a m/e ratio of 1,019.

EXAMPLE 40

Production of [X]

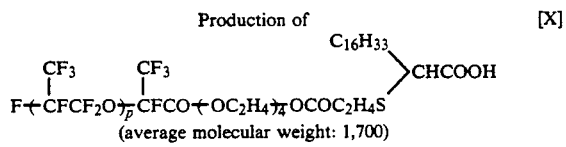
(average molecular weight: 1,700)

There was obtained 125 g of a wax-like semisolid by the same production process as in Example 38, except for using 138 g (0.10 mole) of an acrylate having a fluoroalkyl ether group represented by the formula F$-$(CF(CF$_3$)CF$_2$O$-$)$_p$CF(CF$_3$)CO$-$(OC$_2$H$_4$$-$)$_4$OCOCH=CH$_2$ wherein p is an integer of 1 to 15 (average molecular weight: 1,380) and 31.7 g (0.10 mole) of α-mercaptostearic acid as starting materials. As a result of IR, GPC and FD-MS, the wax-like semisolid was found to be a fluorine-containing compound of the formula X which did not contain the starting materials and any by-product.

IR: There appeared an absorption peak due to a carboxylic acid at 1,705 cm$^{-1}$, an absorption peak due to an ester at 1,755 cm$^{-1}$. There disappeared an absorption peak due to the thiol at 2,600 cm$^{-1}$ and an absorption peak due to a carbon-carbon double bond at 1,640 cm$^{-1}$.

GPC: There were not detected the starting materials, i.e., the acrylate having a fluoroalkyl ether group and α-mercaptostearic acid.

FD-MS: A parent peak appeared at a m/e ratio of 1,700.

EXAMPLE 41

Production of

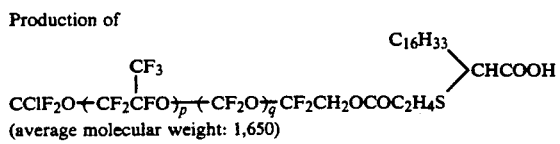
(average molecular weight: 1,650)

There was obtained 142 g of a wax-like semisolid by the same production process as in Example 38, except for using 133 g (0.10 mole) of an acrylate having a fluoroalkyl ether group represented by the formula CClF$_2$O$-$(CF$_2$CF(CF$_3$)O$-$)$_p$(CF$_2$O$-$)$_q$CF$_2$CH$_2$OCOCH=CH$_2$ wherein each of p and q is an integer of 1 to 15 (average molecular weight: 1,330) and 31.7 g (0.10 mole) of α-mercaptostearic acid as starting materials. As a result of IR, GPC and FD-MS, the wax-like semisolid was found to be a fluorine-containing compound of the formula Y which did not contain the starting materials and any by-product.

IR: There appeared an absorption peak due to a carboxylic acid at 1,705 cm$^{-1}$ and an absorption peak due to an ester at 1,755 cm$^{-1}$. There disappeared an absorption peak due to the thiol at 2,600 cm$^{-1}$ and an absorption peak due to a carbon-carbon double bond at 1,640 cm$^{-1}$.

GPC: There were not detected the starting materials, i.e., the acrylate having a fluoroalkyl ether group and α-mercaptostearic acid.

FD-MS: A parent peak appeared at a m/e ratio of 1,650.

EXAMPLE 42

The following fluorine-containing compound was produced under the same conditions as in Example 38.

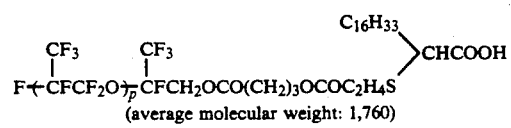
(average molecular weight: 1,760)

EXAMPLE 43

The following fluorine-containing compound was produced under the same conditions as in Example 38.

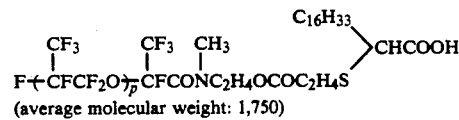
(average molecular weight: 1,750)

EXAMPLE 44

The following fluorine-containing compound was produced under the same condition as in Example 38.

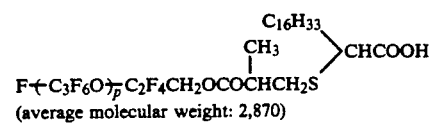
(average molecular weight: 2,870)

EXAMPLE 45

The following fluorine-containing compound was produced under the same conditions as in Example 38.

[Y]

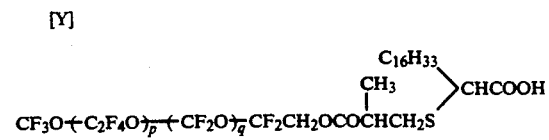

-continued
(average molecular weight: 1,150)

EXAMPLE 46

The following fluorine-containing compound was produced under the same conditions as in Example 38.

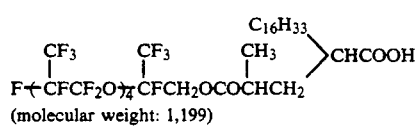
(molecular weight: 1,199)

EXAMPLE 47

The following fluorine-containing compound was produced under the same conditions as in Example 38.

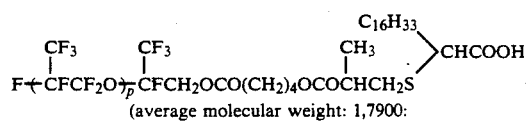
(average molecular weight: 1,7900:

EXAMPLE 48

The following fluorine-containing compound was produced under the same conditions as in Example 38.

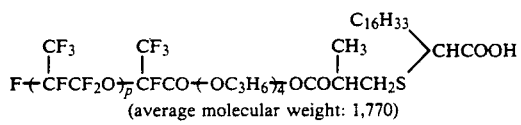
(average molecular weight: 1,770)

EXAMPLE 49

The following fluorine-containing compound was produced under the same conditions as in Example 38.

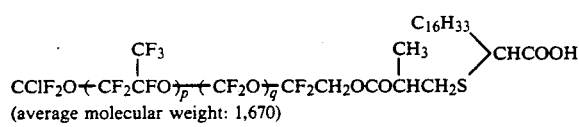
(average molecular weight: 1,670)

EXAMPLES 50 TO 110

There was used a non-magnetic substrate composed of a polyester film and steep hill-shaped protuberances formed on the surface of the film in a number of $1 \times 10^7$ per mm$^2$: in the polyester film, granular protuberances with a gentle slope (average height 70 Å, diameter 1 μm) formed by silica particles contained in the polyester film were present in a number of several protuberances per 100 μm$^2$ of the film surface, and relatively large protruberances formed by fine particles attributable to the residue of a polymerization catalyst had been reduced as such as possible; and the hill-shaped protuberances had been formed by using silica colloidal particles having a diameter of 150 Å as cores and a ultraviolet-curable epoxy resin as a binder. A thin Co-Ni ferromagnetic metal film (Ni content 20%, film thickness 1000 Å) was formed on the substrate in the presence of a slight amount of oxygen by a continuous vacuum oblique deposition method. The oxygen content of the thin film was 5% in terms of atomic fraction.

Each of the above-mentioned fluorine-containing compounds of the present invention or a mixture of the compound and a conventional lubricant was applied on the thin metal film in an amount of 10 mg per m$^2$ of the surface of the thin metal film to form a lubricant layer. Then, the substrate thus treated was cut into a predetermined width to form a magnetic tape. Each of the magnetic tapes thus obtained was set in a commercially available video deck and its output characteristics during repeated running were measured in circumstances of 23° C. and 5% RH. In detail, there was counted the number of runnings which could be conducted until the RF output became lower than its initial value by 3 dB or the output began to vary. Table 1 shows the results obtained. The fluorine-containing compounds of the present invention used are denoted in Table 1 by the above example numbers. Table 1 also shows the measurement results obtained in the case of forming a lubricant layer by the use of a mixture of the fluorine-containing compound of the present invention and a conventional lubricant.

From Table 1, it can be seen that all of the magnetic tape samples having a lubricant layer comprising the fluorine-containing compound of the present invention are excellent in durability in repeated running at a low humidity. On the other hand, as shown for Comparative Examples 1 to 5, the magnetic tape samples having a lubricant layer comprising a conventional lubricant alone are poor in durability at a low humidity.

TABLE 1

| Magnetic tape | Compound of the invention (A) | Conventional lubricant (B) | Mixing ratio (A):(B) | The number of repetitions of running which a magnetic tape endured |
|---|---|---|---|---|
| Example 50 | Compound obtained in Example 1 | — | — | 200 times or more |
| Example 51 | Compound obtained in Example 1 | C$_7$F$_{15}$C$_2$H$_4$ \>NH C$_{14}$H$_{29}$ | 2:1 | 200 times or more |
| Example 52 | Compound | — | — | 200 times |

TABLE 1-continued

| Magnetic tape | Composition of lubricant layer | | | The number of repetitions of running which a magnetic tape endured |
|---|---|---|---|---|
| | Compound of the invention (A) | Conventional lubricant (B) | Mixing ratio (A):(B) | |
| | obtained in Example 2 | | | or more |
| Example 53 | Compound obtained in Example 2 | $C_{17}H_{35}COOC_2H_4C_8F_{17}$ | 1:1 | 200 times or more |
| Example 54 | Compound obtained in Example 3 | — | — | 200 times or more |
| Example 55 | Compound obtained in Example 4 | — | — | 200 times or more |
| Example 56 | Compound obtained in Example 5 | — | — | 200 times or more |
| Example 57 | Compound obtained in Example 6 | — | — | 200 times or more |
| Example 58 | Compound obtained in Example 7 | — | — | 200 times or more |
| Example 59 | Compound obtained in Example 8 | — | — | 200 times or more |
| Example 60 | Compound obtained in Example 9 | — | — | 200 times or more |
| Example 61 | Compound obtained in Example 9 | $\begin{array}{c}C_7F_{15}C_2H_4\\ \phantom{C_7F_{15}}\diagdown\!\!\text{NH}\\ C_{14}H_{29}\diagup\end{array}$ | 2:1 | 200 times or more |
| Example 62 | Compound obtained in Example 10 | — | — | 200 times or more |
| Example 63 | Compound obtained in Example 10 | $C_{17}H_{35}COOC_2H_4C_8F_{17}$ | 1:1 | 200 times or more |
| Example 64 | Compound obtained in Example 11 | — | — | 200 times or more |
| Example 65 | Compound obtained in Example 12 | — | — | 200 times or more |
| Example 66 | Compound obtained in Example 13 | — | — | 200 times or more |
| Example 67 | Compound obtained in Example 14 | — | — | 200 times or more |
| Example 68 | Compound obtained in Example 15 | — | — | 200 times or more |
| Example 69 | Compound obtained in Example 16 | — | — | 200 times or more |
| Example 70 | Compound obtained in Example 16 | $\begin{array}{c}C_7F_{15}C_2H_4\\ \phantom{C_7F_{15}}\diagdown\!\!\text{NH}\\ C_{14}H_{29}\diagup\end{array}$ | 2:1 | 200 times or more |
| Example 71 | Compound obtained in Example 17 | — | — | 200 times or more |
| Example 72 | Compound obtained in Example 17 | $C_{17}H_{35}COOC_2H_4C_8F_{17}$ | 1:1 | 200 times or more |
| Example 73 | Compound obtained in Example 18 | — | — | 200 times or more |
| Example 74 | Compound obtained in Example 19 | — | — | 200 times or more |
| Example 75 | Compound obtained in | | | 200 times or more |

TABLE 1-continued

| Magnetic tape | Composition of lubricant layer | | Mixing ratio (A):(B) | The number of repetitions of running which a magnetic tape endured |
|---|---|---|---|---|
| | Compound of the invention (A) | Conventional lubricant (B) | | |
| | Example 20 | | | |
| Example 76 | Compound obtained in Example 20 | $C_7F_{15}C_2H_4$ $\diagdown$ NH $C_{14}H_{29}$ $\diagup$ | 2:1 | 200 times or more |
| Example 77 | Compound obtained in Example 21 | — | — | 200 times or more |
| Example 78 | Compound obtained in Example 21 | $C_{17}H_{35}COOC_2H_4C_8F_{17}$ | 1:1 | 200 times or more |
| Example 79 | Compound obtained in Example 22 | — | — | 200 times or more |
| Example 80 | Compound obtained in Example 23 | — | — | 200 times or more |
| Example 81 | Compound obtained in Example 24 | — | — | 200 times or more |
| Example 82 | Compound obtained in Example 25 | — | — | 200 times or more |
| Example 83 | Compound obtained in Example 26 | — | — | 200 times or more |
| Example 84 | Compound obtained in Example 27 | — | — | 200 times or more |
| Example 85 | Compound obtained in Example 28 | — | — | 200 times or more |
| Example 86 | Compound obtained in Example 29 | — | — | 200 times or more |
| Example 87 | Compound obtained in Example 30 | — | — | 200 times or more |
| Example 88 | Compound obtained in Example 31 | — | — | 200 times or more |
| Example 89 | Compound obtained in Example 31 | $C_7F_{15}C_2H_4$ $\diagdown$ NH $C_{14}H_{29}$ $\diagup$ | 2:1 | 200 times or more |
| Example 90 | Compound obtained in Example 32 | — | — | 200 times or more |
| Example 91 | Compound obtained in Example 32 | $C_{17}H_{35}COOC_2H_4C_8F_{17}$ | 1:1 | 200 times or more |
| Example 92 | Compound obtained in Example 33 | — | — | 200 times or more |
| Example 93 | Compound obtained in Example 34 | — | — | 200 times or more |
| Example 94 | Compound obtained in Example 35 | — | — | 200 times or more |
| Example 95 | Compound obtained in Example 36 | — | — | 200 times or more |
| Example 96 | Compound obtained in Example 37 | — | — | 200 times or more |
| Example 97 | Compound obtained in Example 38 | — | — | 200 times or more |

TABLE 1-continued

| Magnetic tape | Composition of lubricant layer | | | The number of repetitions of running which a magnetic tape endured |
|---|---|---|---|---|
| | Compound of the invention (A) | Conventional lubricant (B) | Mixing ratio (A):(B) | |
| Example 98 | Compound obtained in Example 38 | $C_7F_{15}C_2H_4$ $\diagdown$ NH $C_{14}H_{29}$ $\diagup$ | 2:1 | 200 times or more |
| Example 99 | Compound obtained in Example 39 | — | — | 200 times or more |
| Example 100 | Compound obtained in Example 39 | $C_{17}H_{35}COOC_2H_4C_8F_{17}$ | 1:1 | 200 times or more |
| Example 101 | Compound obtained in Example 40 | — | — | 200 times or more |
| Example 102 | Compound obtained in Example 41 | — | — | 200 times or more |
| Example 103 | Compound obtained in Example 42 | — | — | 200 times or more |
| Example 104 | Compound obtained in Example 43 | — | — | 200 times or more |
| Example 105 | Compound obtained in Example 44 | — | — | 200 times or more |
| Example 106 | Compound obtained in Example 45 | — | — | 200 times or more |
| Example 107 | Compound obtained in Example 46 | — | — | 200 times or more |
| Example 108 | Compound obtained in Example 47 | — | — | 200 times or more |
| Example 109 | Compound obtained in Example 48 | — | — | 200 times or more |
| Example 110 | Compound obtained in Example 49 | — | — | 200 times or more |
| Comparative Example 1 | — | $C_7F_{15}C_2H_4$ $\diagdown$ NH $C_{14}H_{29}$ $\diagup$ | — | 20 times |
| Comparative Example 2 | — | $C_{17}H_{35}COOC_2H_4C_8F_{17}$ | — | 33 times |
| Comparative Example 3 | — | $CF_3$ $\mid$ F$\mathord{\leftarrow}$CFCF$_2$O$\mathord{\rightarrow}_{\overline{p}}$CF$_2$COOH (average molecular weight: 2,000) | — | 57 times |
| Comparative Example 4 | — | $CF_3$ $CF_3$ $CH_3$ $\mid$ $\mid$ $\mid$ $C_3F_7OCFCF_2OCFCONCH_2COOH$ | — | 50 times |
| Comparative Example 5 | — | $CF_3$ $CF_3$ $C_{12}H_{25}$ $\mid$ $\mid$ $\mid$ $C_3F_7OCFCF_2OCFCONCH_2COOH$ | — | 92 times |

EXAMPLES 111 TO 171

A plated non-magnetic Ni-P alloy film of 25 μm in thickness was formed on the surface of an Al alloy plate having a diameter of 95 mm and a thickness of 1.2 mm, and protuberances were formed in the surface of the film by texturing so as to adjust the average roughness of the surface to 50 Å and the maximum height of the protuberances to 300 Å, whereby a non-magnetic substrate was obtained. A Cr primer layer of 1,300 Å in thickness and a thin Co-Ni ferromagnetic metal film of 600 Å in thickness were formed on the substrate by sputtering. A graphite protective layer of 200 Å in thickness was further formed on the thin metal film by sputtering. Thus, sample A was obtained. Sample B was obtained in the same manner as above except for forming a diamond-like carbon protective layer of 50 Å in thickness by plasma CVD in place of the graphite protective layer. Each of the above-mentioned fluorine-containing compounds of the present invention or a mixture of the compound and a conventional lubricant was applied on the protective layer of each of these samples in an amount of 10 mg per m$^2$ of the surface of the protective layer to form a lubricant layer. The magnetic discs thus obtained were subjected to a CSS endurance test in circumstances of 23° C. and 5% RH, and the durability was judged by the number of times of CSS at the time when the coefficient of friction exceeded 1.0 or when head crush occurred. Table 2 shows the results obtained. The fluorine-containing compounds of the present invention used are denoted in Table 2 by the above example numbers. Table 2 also shows the test results obtained in the case of forming a lubricant layer by the use of a mixture of the fluorine-containing compound of the present invention and a conventional lubricant.

From Table 2, it can be seen that all of the magnetic disc samples having a lubricant layer comprising the fluorine-containing compound of the present invention are excellent in CSS durability at a low humidity. On the other hand, as shown for Comparative Examples 6 to 10, magnetic disc samples having a lubricant layer comprising a conventional lubricant alone are poor in durability at a low humidity.

TABLE 2

| Magnetic disc | Compound of the invention (A) | Conventional lubricant (B) | Mixing ratio (A):(B) | Sample | The number of repetitions of CSS which a magnetic disc endured |
|---|---|---|---|---|---|
| Example 111 | Compound obtained in Example 1 | — | — | A | 50,000 times or more |
| Example 112 | Compound obtained in Example 1 | $C_7F_{15}C_2H_4$ $\diagdown$ NH $C_{14}H_{29}$ $\diagup$ | 2:1 | B | 50,000 times or more |
| Example 113 | Compound obtained in Example 2 | — | — | B | 50,000 times or more |
| Example 114 | Compound obtained in Example 2 | $C_{17}H_{35}COOC_2H_4C_8F_{17}$ | 1:1 | A | 50,000 times or more |
| Example 115 | Compound obtained in Example 3 | — | — | A | 50,000 times or more |
| Example 116 | Compound obtained in Example 4 | — | — | A | 50,000 times or more |
| Example 117 | Compound obtained in Example 5 | — | — | A | 50,000 times or more |
| Example 118 | Compound obtained in Example 6 | — | — | A | 50,000 times or more |
| Example 119 | Compound obtained in Example 7 | — | — | A | 50,000 times or more |
| Example 120 | Compound obtained in Example 8 | — | — | A | 50,000 times or more |
| Example 121 | Compound obtained in Example 9 | — | — | A | 50,000 times or more |
| Example 122 | Compound obtained in Example 9 | $C_7F_{15}C_2H_4$ $\diagdown$ NH $C_{14}H_{29}$ $\diagup$ | 2:1 | B | 50,000 times or more |
| Example 123 | Compound obtained in Example 10 | — | — | B | 50,000 times or more |
| Example 124 | Compound obtained in Example 10 | $C_{17}H_{35}COOC_2H_4C_8F_{17}$ | 1:1 | A | 50,000 times or more |
| Example 125 | Compound obtained in Example 11 | — | — | A | 50,000 times or more |
| Example 126 | Compound obtained in Example 12 | — | — | A | 50,000 times or more |
| Example 127 | Compound obtained in Example 13 | — | — | A | 50,000 times or more |
| Example 128 | Compound obtained in Example 14 | — | — | A | 50,000 times or more |
| Example 129 | Compound | — | — | A | 50,000 times |

TABLE 2-continued

| Magnetic disc | Composition of lubricant layer | | | Sample | The number of repetitions of CSS which a magnetic disc endured |
|---|---|---|---|---|---|
| | Compound of the invention (A) | Conventional lubricant (B) | Mixing ratio (A):(B) | | |
| | obtained in Example 15 | | | | or more |
| Example 130 | Compound obtained in Example 16 | — | — | A | 50,000 times or more |
| Example 131 | Compound obtained in Example 16 | $C_7F_{15}C_2H_4$ $>$NH $C_{14}H_{29}$ | 2:1 | B | 50,000 times or more |
| Example 132 | Compound obtained in Example 17 | — | — | B | 50,000 times or more |
| Example 133 | Compound obtained in Example 17 | $C_{17}H_{35}COOC_2H_4C_8F_{17}$ | 1:1 | A | 50,000 times or more |
| Example 134 | Compound obtained in Example 18 | — | — | A | 50,000 times or more |
| Example 135 | Compound obtained in Example 19 | — | — | A | 50,000 times or more |
| Example 136 | Compound obtained in Example 20 | — | — | A | 50,000 times or more |
| Example 137 | Compound obtained in Example 20 | $C_7F_{15}C_2H_4$ $>$NH $C_{14}H_{29}$ | 2:1 | B | 50,000 times or more |
| Example 138 | Compound obtained in Example 21 | — | — | B | 50,000 times or more |
| Example 139 | Compound obtained in Example 21 | $C_{17}H_{35}COOC_2H_4C_8F_{17}$ | 1:1 | A | 50,000 times or more |
| Example 140 | Compound obtained in Example 22 | — | — | A | 50,000 times or more |
| Example 141 | Compound obtained in Example 23 | — | — | A | 50,000 times or more |
| Example 142 | Compound obtained in Example 24 | — | — | A | 50,000 times or more |
| Example 143 | Compound obtained in Example 25 | — | — | A | 50,000 times or more |
| Example 144 | Compound obtained in Example 26 | — | — | A | 50,000 times or more |
| Example 145 | Compound obtained in Example 27 | — | — | A | 50,000 times or more |
| Example 146 | Compound obtained in Example 28 | — | — | A | 50,000 times or more |
| Example 147 | Compound obtained in Example 29 | — | — | A | 50,000 times or more |
| Example 148 | Compound obtained in Example 30 | — | — | A | 50,000 times or more |
| Example 149 | Compound obtained in Example 31 | — | — | A | 50,000 times or more |
| Example 150 | Compound obtained in Example 31 | $C_7F_{15}C_2H_4$ $>$NH $C_{14}H_{29}$ | 2:1 | B | 50,000 times or more |
| Example 151 | Compound obtained in | — | — | B | 50,000 times or more |

TABLE 2-continued

| Magnetic disc | Compound of the invention (A) | Conventional lubricant (B) | Mixing ratio (A):(B) | Sample | The number of repetitions of CSS which a magnetic disc endured |
|---|---|---|---|---|---|
| Example 152 | Compound obtained in Example 32 | $C_{17}H_{35}COOC_2H_4C_8F_{17}$ | 1:1 | A | 50,000 times or more |
| Example 153 | Compound obtained in Example 32 | — | — | A | 50,000 times or more |
| Example 154 | Compound obtained in Example 33 | — | — | A | 50,000 times or more |
| Example 155 | Compound obtained in Example 34 | — | — | A | 50,000 times or more |
| Example 156 | Compound obtained in Example 35 | — | — | A | 50,000 times or more |
| Example 157 | Compound obtained in Example 36 | — | — | A | 50,000 times or more |
| Example 158 | Compound obtained in Example 37 | — | — | A | 50,000 times or more |
| Example 159 | Compound obtained in Example 38 | $C_7F_{15}C_2H_4$<br>$\phantom{xxxx}$>NH<br>$C_{14}H_{29}$ | 2:1 | B | 50,000 times or more |
| Example 160 | Compound obtained in Example 39 | — | — | B | 50,000 times or more |
| Example 161 | Compound obtained in Example 39 | $C_{17}H_{35}COOC_2H_4C_8F_{17}$ | 1:1 | A | 50,000 times or more |
| Example 162 | Compound obtained in Example 40 | — | — | A | 50,000 times or more |
| Example 163 | Compound obtained in Example 41 | — | — | A | 50,000 times or more |
| Example 164 | Compound obtained in Example 42 | — | — | A | 50,000 times or more |
| Example 165 | Compound obtained in Example 43 | — | — | A | 50,000 times or more |
| Example 166 | Compound obtained in Example 44 | — | — | A | 50,000 times or more |
| Example 167 | Compound obtained in Example 45 | — | — | A | 50,000 times or more |
| Example 168 | Compound obtained in Example 46 | — | — | A | 50,000 times or more |
| Example 169 | Compound obtained in Example 47 | — | — | A | 50,000 times or more |
| Example 170 | Compound obtained in Example 48 | — | — | A | 50,000 times or more |
| Example 171 | Compound obtained in Example 49 | — | — | A | 50,000 times or more |
| Comparative Example 6 | — | $C_7F_{15}C_2H_4$<br>$\phantom{xxxx}$>NH<br>$C_{14}H_{29}$ | — | A | Crushed by 5,000 repetitions |
| Comparative Example 7 | — | $C_{17}H_{35}COOC_2H_4C_8F_{17}$ | — | A | Crushed by 5,000 repetitions |

TABLE 2-continued

| Magnetic disc | Composition of lubricant layer | | | Sample | The number of repetitions of CSS which a magnetic disc endured |
|---|---|---|---|---|---|
| | Compound of the invention (A) | Conventional lubricant (B) | Mixing ratio (A):(B) | | |
| Comparative Example 8 | — | F-(CFCF$_2$O)$_{\overline{p}}$CF$_2$COOH with CF$_3$ branch (average molecular weight: 2,000) | — | A | 10,000 times |
| Comparative Example 9 | — | C$_3$F$_7$OCFCF$_2$OCFCONCH$_2$COOH with CF$_3$, CF$_3$, CH$_3$ branches | — | A | 8,000 times |
| Comparative Example 10 | — | C$_3$F$_7$OCFCF$_2$OCFCONCH$_2$COOH with CF$_3$, CF$_3$, C$_{12}$H$_{25}$ branches | — | A | 20,000 times |

What is claimed is:

1. A fluorine-containing compound represented by the formula (II):

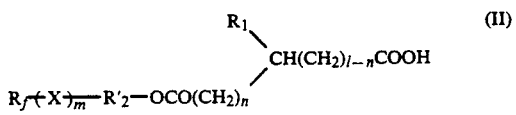

wherein $R_f$ is a fluoroalkyl ether end group having 5 to 50 carbon atoms, $R_1$ is an aliphatic alkyl end group or an aliphatic alkenyl end group, $R'_2$ is an aliphatic alkylene group or an aliphatic polyalkylene oxide group, X is a connecting group selected from the group consisting of —COOR$_5$— and —CON(R$_6$)—, $R_5$ is an aliphatic alkylene group having no or one or more carbon atoms, $R_6$ is hydrogen or an aliphatic alkyl group having 1 to 12 carbon atoms and each of m and n is zero or 1.

2. A compound according to claim 1, wherein X is —COOR$_5$—.

3. A lubricant composition comprising a lubricatingly effective amount of a fluorine-containing compound according to claim 1 and one of a lubricant and a rust preventive.

4. A lubricant composition comprising a lubricatingly effective amount of a fluorine-containing compound according to claim 2 and one of a lubricant and a rust preventive.

5. A fluorine-containing compound represented by the formula (III):

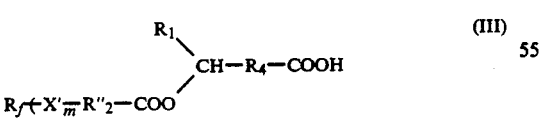

wherein $R_f$ is a fluoroalkyl ether and group having 5 to 50 carbon atoms, $R_1$ is an aliphatic alkyl end group or an aliphatic alkenyl end group, each of $R''_2$ and $R_4$ is an aliphatic alkylene group having no or one or more carbon atoms, X' is a connecting group selected from the group consisting of —COOR'$_5$— and —CON(R$_6$)—, $R'_5$ is an aliphatic alkylene group, $R_6$ is hydrogen or an aliphatic alkyl group having 1 to 12 carbon atoms, and m is zero or 1.

6. A compound according to claim 5, wherein X' is —COOR'$_5$—.

7. A lubricant composition comprising a lubricatingly effective amount of a fluorine-containing compound according to claim 5 and one of a lubricant and a rust preventive.

8. A lubricant composition comprising a lubricatingly effective amount of a fluorine-containing compound according to claim 6 and one of a lubricant and a rust preventive.

9. A fluorine-containing compound represented by the formula (VIII):

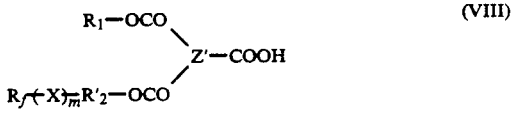

wherein $R_f$ is a fluoroalkyl ether end group having 5 to 50 carbon atoms, $R_1$ is an aliphatic alkyl end group or an aliphatic alkenyl end group, $R'_2$ is an aliphatic alkylene group or an aliphatic polyalkylene oxide group, X is a connecting group selected from the group consisting of —COOR$_5$— and —CON(R$_6$)—, $R_5$ is an aliphatic alkylene group having no or one or more carbon atoms, $R_6$ is hydrogen or an aliphatic alkyl group having 1 to 12 carbon atoms, Z' is a connecting group represented by the formula

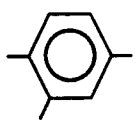

and m is zero or 1.

10. A compound according to claim 9, wherein X is —COOR$_5$—.

11. A lubricant composition comprising a lubricatingly effective amount of a fluorine-containing compound according to claim 9 and one of a lubricant and a rust preventive.

12. A lubricant composition comprising a lubricatingly effective amount of a fluorine-containing compound according to claim 10 and one of a lubricant and a rust preventive.

13. A fluorine-containing compound represented by the formula (IX):

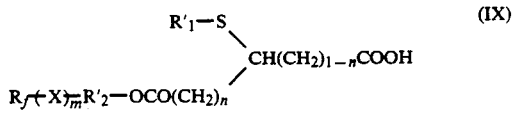

wherein $R_f$ is a fluoroalkyl ether end group having 5 to 50 carbon atoms, $R'_1$ is an aliphatic alkyl end group, $R'_2$ is an aliphatic alkylene group or an aliphatic polyalkylene oxide group, X is a connecting group selected from the group consisting of —COOR$_5$— and CON(R$_6$)—, $R_5$ is an aliphatic alkylene group having no or one or more carbon atoms, $R_6$ is hydrogen or an aliphatic alkyl group having 1 to 12 carbon atoms, and each of m and n is zero or 1.

14. A compound according to claim 13, wherein X is —COOR$_5$—.

15. A lubricant composition comprising a lubricatingly effective amount of a fluorine-containing compound according to claim 13 and one of a lubricant and a rust preventive.

16. A lubricant composition comprising a lubricatingly effective amount of a fluorine-containing compound according to claim 14 and one of a lubricant and a rust preventive.

17. A fluorine-containing compound represented by the formula (X):

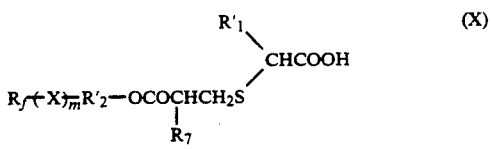

wherein $R_f$ is a fluoroalkyl ether end group having 5 to 50 carbon atoms, $R'_1$ is an aliphatic alkyl end group, $R'_2$ is an aliphatic alkylene group or an aliphatic polyalkylene oxide group, $R_7$ is hydrogen or methyl, X is a connecting group selected from the group consisting of —COOR$_5$— and CON(R$_6$)—, $R_5$ is an aliphatic alkylene group having no or one or more carbon atoms, $R_6$ is hydrogen or an aliphatic alkyl group having 1 to 12 carbon atoms, and m is zero or 1.

18. A compound according to claim 17, wherein X is —COOR$_5$—.

19. A lubricant composition comprising a lubricatingly effective amount of a fluorine-containing compound according to claim 17 and one of a lubricant and a rust preventive.

20. A lubricant composition comprising a lubricatingly effective amount of a fluorine-containing compound according to claim 18 and one of a lubricant and a rust preventive.

* * * * *